(12) United States Patent
Hagen et al.

(10) Patent No.: US 8,731,712 B2
(45) Date of Patent: May 20, 2014

(54) METHOD AND APPARATUS FOR EFFECTING TRANSFER OF REACTION RECEPTACLES IN AN INSTRUMENT FOR MULTI-STEP ANALYTICAL PROCEDURES

(75) Inventors: Norbert D. Hagen, Carlsbad, CA (US); Byron J. Knight, San Diego, CA (US); David Opalsky, San Diego, CA (US); Jason Rhubottom, Oceanside, CA (US); Olaf Hörger, Neuenbürg (DE); Harald Thahedl, Wimsheim (DE); Heiko Sayer, Neuenbürg (DE); Stefan Habrich, Bad Wildbad (DE)

(73) Assignee: Gen-Probe Incorporated, San Diego, CA (US)

( * ) Notice: Subject to any disclaimer, the term of this patent is extended or adjusted under 35 U.S.C. 154(b) by 94 days.

(21) Appl. No.: 13/320,746

(22) PCT Filed: May 17, 2010

(86) PCT No.: PCT/US2010/035143
§ 371 (c)(1),
(2), (4) Date: Jan. 26, 2012

(87) PCT Pub. No.: WO2010/132885
PCT Pub. Date: Nov. 18, 2010

(65) Prior Publication Data
US 2012/0128451 A1 May 24, 2012

Related U.S. Application Data

(60) Provisional application No. 61/178,728, filed on May 15, 2009.

(51) Int. Cl.
*G06F 7/00* (2006.01)

(52) U.S. Cl.
USPC .......... 700/229; 700/230; 700/245; 700/217; 700/214

(58) Field of Classification Search
None
See application file for complete search history.

(56) References Cited

U.S. PATENT DOCUMENTS 5,273,050 A 12/1993 Schaus et al.
5,336,467 A 8/1994 Heidt et al.
(Continued)

FOREIGN PATENT DOCUMENTS

EP 0458138 A2 11/1991
EP 0583098 A1 2/1994
(Continued)

*Primary Examiner* — Yolanda Cumbess
(74) *Attorney, Agent, or Firm* — David L. Devernoe; Charles B. Cappellari; Richard Wydeven

(57) ABSTRACT

Systems for effecting transfer of reaction receptacles between modules of an instrument for performing multi-step analytical procedures and for adjusting for variations in the positions of such modules includes a receptacle carrier supported on a track on which the carrier translates between different modules located adjacent to the track. The carrier includes a receptacle distribution head supported on a receptacle carrier carriage. The distribution head includes a receptacle moving mechanism adapted to move receptacles into and out of the distribution head and into and out of a module. The carriage is engaged with the track and adapted for translation along the track. Drive systems effect powered translation of the carriage, powered elevation and rotation of the distribution head, and powered movement of receptacles into and out of the distribution head. A transfer position locating system automatically determines a receptacle transfer position of the receptacle carrier with respect to each module.

48 Claims, 20 Drawing Sheets

(56) References Cited

U.S. PATENT DOCUMENTS

| | | |
|---|---|---|
| 5,415,840 A | 5/1995 | Sano et al. |
| 5,460,778 A | 10/1995 | Macindoe, Jr. |
| 5,820,055 A | 10/1998 | Leger et al. |
| 5,861,563 A | 1/1999 | Boyd et al. |
| 6,060,022 A | 5/2000 | Pang et al. |
| 6,071,477 A | 6/2000 | Auclair et al. |
| 6,096,561 A | 8/2000 | Tayi |
| 6,148,680 A | 11/2000 | Baeuerle et al. |
| 6,159,425 A | 12/2000 | Edwards et al. |
| 6,162,399 A | 12/2000 | Martinell Gisper-Sauch |
| 6,168,759 B1 | 1/2001 | Green et al. |
| 6,183,186 B1 | 2/2001 | Howells et al. |
| 6,335,166 B1 * | 1/2002 | Ammann et al. ............ 435/6.11 |
| 6,426,044 B1 | 7/2002 | Cohen et al. |
| 6,649,128 B1 | 11/2003 | Meyer et al. |
| 6,764,648 B1 | 7/2004 | Roach et al. |
| 6,764,649 B2 | 7/2004 | Ammann |
| 6,866,461 B2 | 3/2005 | DeWinter et al. |
| 6,889,813 B1 | 5/2005 | Trammell et al. |
| 6,913,934 B2 | 7/2005 | DeWinter et al. |
| 6,974,294 B2 | 12/2005 | Pressman et al. |
| 7,118,892 B2 | 10/2006 | Ammann et al. |
| 7,201,072 B1 | 4/2007 | Wiederin et al. |
| 7,220,385 B2 | 5/2007 | Blecka et al. |
| 7,228,198 B2 | 6/2007 | Vollm et al. |
| 2004/0179923 A1 | 9/2004 | Beach et al. |

FOREIGN PATENT DOCUMENTS

| | | |
|---|---|---|
| FR | 2630216 A1 | 10/1989 |
| GB | 2383183 A | 6/2003 |
| JP | 01257342 | 10/1989 |
| JP | 06329208 | 11/1994 |
| JP | 2004028963 | 1/2004 |
| JP | 2004055697 | 2/2004 |
| JP | 2005255244 | 9/2005 |
| WO | 9401780 A2 | 1/1994 |
| WO | 9401781 A1 | 1/1994 |
| WO | 9801760 A2 | 1/1998 |
| WO | 9850158 A1 | 11/1998 |
| WO | 03008103 A1 | 1/2003 |
| WO | 2005005992 A2 | 1/2005 |
| WO | 2005093433 A1 | 10/2005 |

* cited by examiner

METHOD AND APPARATUS FOR EFFECTING TRANSFER OF REACTION RECEPTACLES IN AN INSTRUMENT FOR MULTI-STEP ANALYTICAL PROCEDURES

CROSS-REFERENCE TO RELATED APPLICATIONS

This application is the National Stage pursuant to 35 U.S.C. §371 of PCT International Application No. PCT/US10/35143, which claims the benefit of U.S. Provisional Application No. 61/178,728, filed on May 15, 2009, the disclosure of each of which is incorporated by reference herein in its entirety.

FIELD OF THE INVENTION

The present invention relates to systems, methods and apparatus for effecting transfer of reaction receptacles between modules of an instrument for performing multi-step analytical procedures and for automatically adjusting for variations in the positions of such modules.

BACKGROUND OF THE INVENTION

All documents referred to herein, or the indicated portions, are hereby incorporated by reference herein. No document, however, is admitted to be prior art to the claimed subject matter.

Instruments having a variety of modules within which one or more steps of a multi-step procedure are to be performed are known in the art. A challenge in the design and operation of such instruments is devising a way to efficiently transfer the receptacles within which reactions (e.g., chemical, biochemical or biological) take place (hereinafter "reaction receptacles") between the different modules of the instrument. Modules within the instrument are often replaced or removed for servicing and then reinstalled, and thus the precise location of a receptacle transfer position can vary and is not known with complete accuracy. Thus, the precise location at which any device or apparatus for transferring reaction receptacles between modules must be positioned may not be accurately known.

SUMMARY OF THE INVENTION

Aspects of the invention are embodied in an apparatus for transferring one or more receptacles between a plurality of receptacle-receiving structures. The apparatus comprise a transport track, a receptacle carrier, and a transfer position locating system. The transport track has opposed ends, and the receptacle-receiving structures are disposed at different locations adjacent to the transport track. The receptacle carrier, which is operatively engaged with the transport track, is adapted to carry a receptacle and translate along the transport track in a first or second direction between the opposed ends of the track. The receptacle carrier is further adapted to selectively stop at a transfer position with respect to any of the receptacle-receiving structures disposed adjacent the transport track, and the receptacle carrier includes a receptacle moving mechanism that is adapted to move a receptacle with respect to the receptacle carrier to move a receptacle into the receptacle carrier, out of the receptacle carrier, or alternately into and out of the receptacle carrier. The transfer position locating system is adapted to automatically determine, for each receptacle-receiving structure, a location of a transfer position of the receptacle carrier with respect to the receptacle-receiving structure to enable the receptacle carrier to transfer a receptacle between the receptacle carrier and the receptacle-receiving structure.

According to other aspects of the invention, the transport track comprises a base portion and an upright backing portion and a guide track mounted on the base portion and a guide rail mounted to the upright portion. A portion of the receptacle carrier is engaged with the guide track and the guide rail. In certain embodiments, the transport track is linear, and in certain embodiments, the transport track is substantially horizontal.

According to further aspects of the invention, the apparatus comprises a carrier translation system adapted to effect powered translation of the receptacle carrier along the transport track, a carrier elevation system adapted to move at least a portion of the receptacle carrier in a transverse direction with respect to the transport track, and/or a carrier rotation system adapted to rotate at least a portion of the receptacle carrier about an axis of rotation.

In one embodiment, the carrier translation system comprises a translation drive motor having an output shaft, a carrier drive belt coupled to the receptacle carrier, and one or more pulleys supporting the carrier drive belt. The carrier drive belt is coupled to the output shaft of the translation drive motor so that rotation of the output shaft is transmitted via the carrier drive belt into translation of the receptacle carrier along the transport track.

In one embodiment, the apparatus includes encoder coupled to the translation drive motor for monitoring rotations of the output shaft.

In one embodiment, the apparatus includes a belt tensioner configured to impart tension in the carrier drive belt.

In one embodiment, the apparatus comprises a carrier position sensor configured to detect when the receptacle carrier is in a specified position on the transport track.

In one embodiment, the transport track is substantially horizontal, and the carrier elevation system is adapted to move at least a portion of the receptacle carrier in a vertical direction with respect to the transport track.

In one embodiment, the carrier elevation system comprises an elevation drive motor having an output shaft, a drive screw shaft having a longitudinal axis and operatively coupled to the elevation drive motor for powered rotation of the drive screw shaft, and an elevation block coupled to the drive screw shaft such that rotation of the drive screw shaft causes translation of the elevation block along the longitudinal axis of the drive screw shaft, and at least a portion of the receptacle carrier is carried on the elevation block.

In one embodiment, the apparatus comprises an encoder coupled to the elevation drive motor for monitoring rotations of the output shaft.

In one embodiment, the apparatus includes elevation position sensor configured to detect when at least a portion of the receptacle carrier is in a specified transverse distance from the transport track.

In one embodiment, the transport track is substantially horizontal and the carrier rotation system is adapted to rotate the receptacle carrier about an axis of rotation that is substantially vertical.

In one embodiment, the carrier rotation system includes a rotation drive motor having an output shaft, a drive gear coupled to the output shaft, and a platform gear mounted so as to be rotatable about the axis of rotation and coupled to the drive gear for powered rotation to the platform gear, and at least a portion of the receptacle carrier is carried on the platform gear. In one embodiment, the apparatus further includes an encoder coupled to the rotation drive motor for monitoring rotations of the output shaft.

In one embodiment, the apparatus further includes a rotation position sensor configured to detect when at least a portion of the receptacle carrier is in a specified rotational position about the axis of rotation.

In one embodiment, the receptacle moving mechanism includes a receptacle engagement device configured to releasably engage a receptacle to permit physical manipulation of the engaged receptacle and a receptacle drive motor having an output shaft coupled to the receptacle engagement device for effecting powered movement of the receptacle engagement device.

In one embodiment, the receptacle engagement device comprises a hook.

In one embodiment, the receptacle engagement device is carried on an engagement device carriage, and the receptacle moving mechanism further includes a receptacle guide rail on which the engagement device carriage is translatably carried, a receptacle drive belt coupled to the engagement device carriage, and one or more pulleys supporting the receptacle drive belt. The receptacle drive belt is coupled to the output shaft of the receptacle drive motor so that rotation of the output shaft is transmitted via the receptacle drive belt into translation of the engagement device carriage along the receptacle guide rail.

In one embodiment, the apparatus further includes an encoder coupled to the receptacle drive motor for monitoring rotations of the output shaft.

In one embodiment, the apparatus further includes a belt tensioner configured to impart tension to the receptacle drive belt.

In one embodiment, the apparatus further includes an engagement device position sensor configured to detect when the engagement device carriage is in a specified position on the receptacle guide rail.

In one embodiment, the receptacle carrier comprises a receptacle carrier carriage adapted to translate along the transport track and a distribution head supported by the receptacle carrier carriage and configured to receive and hold a receptacle, and the receptacle moving mechanism is disposed within the distribution head. In one embodiment, a carrier translation system is coupled to the receptacle carrier carriage and is adapted to effect powered translation of the receptacle carrier carriage along the transport track. In one embodiment, a carrier elevation system is coupled to the distribution head and is adapted to move the distribution head relative to the receptacle carrier carriage in a direction transverse to the transport track. And in one embodiment a carrier rotation system is coupled to the distribution head and is adapted to rotate the distribution head relative to the receptacle carrier carriage about an axis of rotation.

In one embodiment, the transfer position locating system includes a position locator element associated with the receptacle carrier, one or more signal generators adapted to generate signal data representative of at least one of a position and an orientation of the receptacle carrier, and data storage configured to store signal data from the one or more signal generators when the position locator element associated with the receptacle carrier engages a position locator element associated with the receptacle-receiving structure.

In one embodiment, the position locator element associated with the receptacle carrier comprises a portion of the receptacle carrier that physically contacts a position locator element associated with the receptacle-receiving structure.

In one embodiment, the position locator element associated with the receptacle carrier comprises a receptacle engagement device coupled with the receptacle moving mechanism and configured to releasably engage a receptacle to permit physical manipulation of the engaged receptacle.

In one embodiment, the apparatus further includes a controller in signal communication with the receptacle engagement device to capacitively sense when the receptacle engagement device contacts the position locator element associated with the receptacle-receiving structure.

In an automated apparatus for transferring one or more receptacles between a plurality of receptacle-receiving structures in which the apparatus includes a transport track with the receptacle-receiving structures located adjacent to the transport track and a receptacle carriage operatively engaged with the track and adapted to transport a receptacle along the track and insert a receptacle into or remove a receptacle from a receptacle-receiving structure disposed adjacent to the track, aspects of the invention are embodied in a method for positioning the receptacle carriage with respect to each of the receptacle-receiving structures to enable the receptacle carriage to transfer a receptacle between the receptacle carriage and each of the receptacle-receiving structures. The method comprises the steps of (a) moving the receptacle carriage along the track to an approximate location of one of the receptacle-receiving structures and then (b) moving the receptacle carriage with respect to the receptacle-receiving structure in two or more directions until a position locator element associated with the receptacle carriage engages a position locator element associated with the receptacle-receiving structure. Engagement of the position locator element associated with the receptacle carriage with the position locator element associated with the receptacle-receiving structure identifies a transfer position of the receptacle carriage with respect to the receptacle-receiving structure to enable the receptacle carriage to transfer a receptacle between the receptacle carriage and the receptacle-receiving structure. In step (c), data relating to the transfer position for the receptacle-receiving structure is stored. In step (d), steps (a)-(c) are repeated for each of the receptacle-receiving structures. In step (e), the receptacle carriage is positioned with respect to each receptacle-receiving structure to enable the receptacle carriage to transfer a receptacle between the receptacle carriage and the receptacle-receiving structure by retrieving the stored transfer position data associated with a receptacle-receiving structure and moving the receptacle carriage to the transfer position defined by the retrieved transfer position data.

In one embodiment, moving the receptacle carriage with respect to the receptacle-receiving structure in two or more directions includes moving the receptacle carriage along the track and moving the receptacle carriage in at least one direction transverse to the direction of the track.

In one embodiment, moving the receptacle carriage with respect to the receptacle-receiving structure in two or more directions further comprises rotating the receptacle carriage about an axis of rotation and moving a receptacle-engaging element of the receptacle carriage in a radial direction with respect to the axis of rotation.

In one embodiment, the receptacle carriage is moved with respect to the receptacle-receiving structure until a portion of the receptacle carriage physically contacts a portion of the receptacle-receiving structure.

In one embodiment, physical contact of a portion of the receptacle carriage with a portion of the receptacle-receiving structure is determined by capacitive sensing.

Aspects of the invention are embodied in an apparatus for transferring one or more receptacles between a plurality of receptacle-receiving structures, one or more of the receptacle receiving structures including a receptacle transfer portal through which a receptacle is placed into or removed from the receptacle-receiving structure and a door disposed over the receptacle transfer portal. The apparatus comprises a receptacle carriage and a carriage positioning system. The receptacle carriage is adapted to carry a receptacle and to selectively stop at a transfer position with respect to any of the receptacle-receiving structures. The receptacle carriage includes a receptacle moving mechanism adapted to move a receptacle with respect to the receptacle carriage to move a receptacle into the receptacle carriage, move a receptacle out of the receptacle carriage, or alternately move a receptacle into and out of the receptacle carriage. A portion of the receptacle carriage is adapted to engage a door of a receptacle-receiving structure and open the door upon performance of a predetermined movement of the receptacle carriage with respect to the receptacle-receiving structure. The carriage positioning system is adapted to automatically position the receptacle carriage so that a portion of the receptacle carriage engages a door of a selected one of the receptacle-receiving structures and to effect the predetermined movement of the receptacle carriage to open the door.

In one embodiment, the apparatus further includes a transfer position locating system adapted to automatically determine, for each receptacle-receiving structure, a location of a transfer position of the receptacle carriage with respect to the receptacle-receiving structure to enable the receptacle carriage to engage a door of each receptacle-receiving structure.

In one embodiment, the transfer position locating system comprises a position locator element associated with the receptacle carriage, one or more signal generators adapted to generate signal data representative of at least one of a position and an orientation of the receptacle carriage, and data storage configured to store signal data from the one or more signal generators when the position locator element associated with the receptacle carriage engages a position locator element associated with the receptacle-receiving structure.

In one embodiment, the portion of the receptacle carriage adapted to engage the door of the receptacle-receiving structure comprises a bracket projecting from the receptacle carriage and configured to engage by contact an actuating element extending from the door.

In one embodiment, a portion of the receptacle carriage is adapted to engage a door of a receptacle-receiving structure and open the door upon performance of a lateral movement of the receptacle carriage to move the door laterally from a closed position to an open position with respect to the receptacle transport portal.

In one embodiment, a portion of the receptacle carriage is adapted to remain engaged with the door of the receptacle-receiving structure, after the predetermined movement of the receptacle carriage, to hold the door in an open position with respect to the receptacle transport portal while the receptacle carriage moves a receptacle through the receptacle transport portal.

In an automated apparatus for transferring one or more receptacles between a plurality of receptacle-receiving structures, wherein the apparatus includes a receptacle carriage adapted to transport a receptacle relative to the receptacle-receiving structures and insert a receptacle into or remove a receptacle from a receptacle-receiving structure, one or more of the receptacle receiving structures including a receptacle transfer portal through which a receptacle is placed into or removed from the receptacle-receiving structure and a door disposed over the receptacle transfer portal, aspects of the invention are embodied in a method for opening a door over a receptacle transfer portal using the receptacle carriage. The method comprises the step of positioning the receptacle carriage so that a portion of the receptacle carriage that is adapted to engage a door of a receptacle-receiving structure and to open the door upon performance of a predetermined movement of the receptacle carriage with respect to the receptacle-receiving structure engages a door of one of the receptacle-receiving structures. Next the predetermined movement of the receptacle carriage is effected to open the door.

In one embodiment, positioning the receptacle carriage comprises the steps of (a) moving the receptacle carriage to an approximate location of one of the receptacle-receiving structures and (b) moving the receptacle carriage with respect to the receptacle-receiving structure in two or more directions until a position locator element associated with the receptacle carriage engages a position locator element associated with the receptacle-receiving structure. Engagement of the position locator element associated with the receptacle carriage with the position locator element associated with the receptacle-receiving structure identifies a transfer position of the receptacle carriage with respect to the receptacle-receiving structure to enable the receptacle carriage to engage a door of the receptacle-receiving structure. In step (c), data relating to the transfer position for the receptacle-receiving structure is stored. In step (d), steps (a)-(c) are repeated for each of the receptacle-receiving structures. And in step (e), the receptacle carriage is positioned with respect to each receptacle-receiving structure to enable the receptacle carriage to engage the door of each receptacle carriage by retrieving the stored transfer position data associated with a receptacle-receiving structure and moving the receptacle carriage to the transfer position defined by the retrieved transfer position data.

In one embodiment, the portion of the receptacle carriage adapted to engage the door of the receptacle-receiving structure comprises a bracket projecting from the receptacle carriage and configured to engage by contact an actuating element extending from the door, and positioning the receptacle carriage comprises moving the receptacle carriage to a position at which the bracket engages the actuating element of the door.

In one embodiment, effecting the predetermined movement comprises moving the receptacle carriage laterally to move the door laterally from a closed position to an open position with respect to the receptacle transport portal.

In one embodiment, the method further includes, after effecting the predetermined movement, maintaining a position of the receptacle carriage engaged with the door of the receptacle-receiving structure to hold the door in an open position with respect to the receptacle transport portal while the receptacle carriage moves a receptacle through the receptacle transport portal.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PREFERRED EMBODIMENT

Overview

Figure 1:
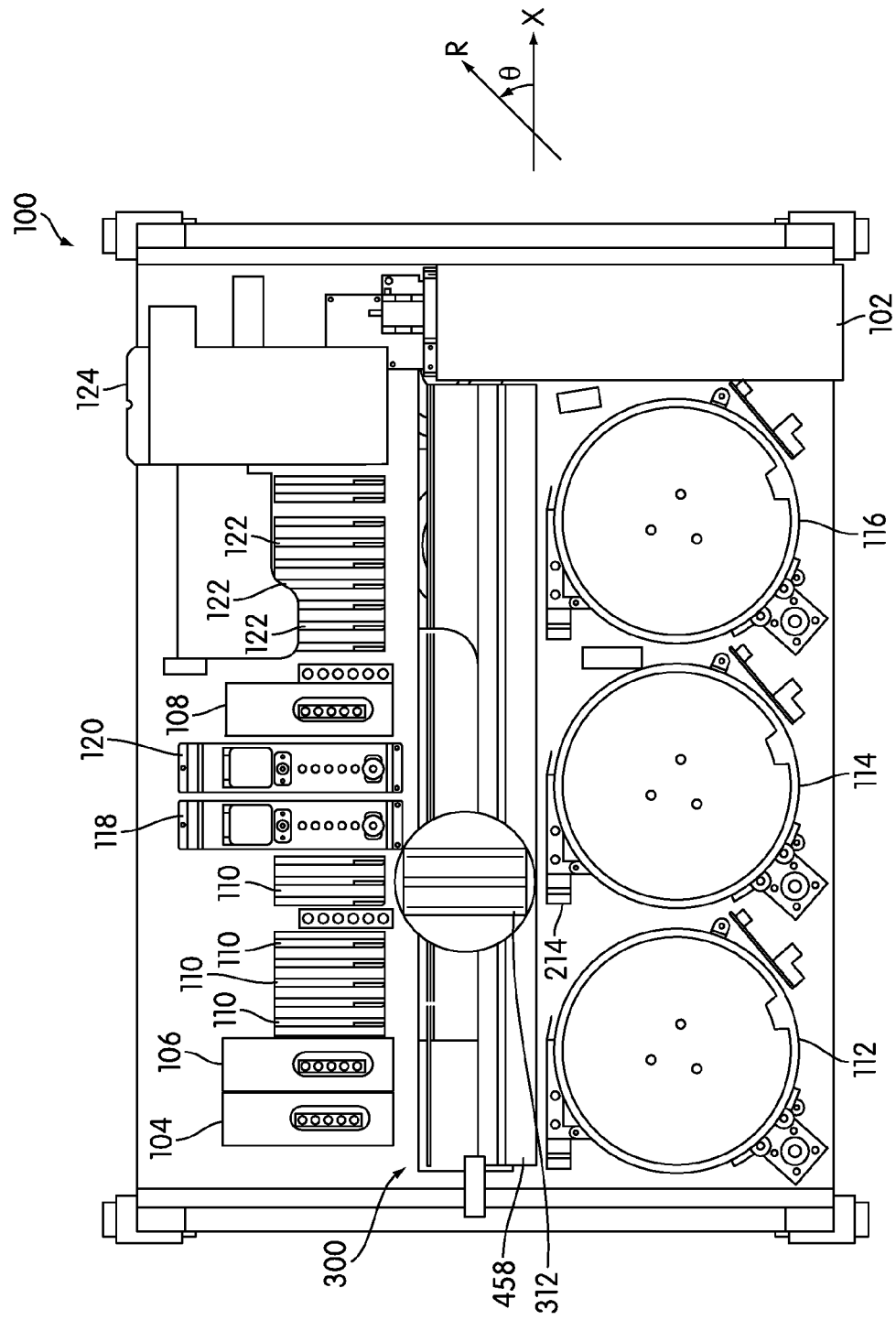
FIG. 1 is a plan view of an analyzer including various modules configured to receive one or more reaction receptacles and within each of which is performed one or more steps of a molecular assay, or other biological or chemical process, and a receptacle transfer apparatus for transferring reaction receptacles between the various modules and insert reaction receptacles into and removing reaction receptacles from the modules.

An analyzer in which the method and apparatus of the present invention may be implemented is shown schematically in plan view and designated by reference number 100 in FIG. 1. The analyzer 100 includes various modules configured to receive one or more reaction receptacles (described in more detail below) within each of which is performed one or more steps of a multi-step analytical process, such as a nucleic acid test (NAT), or other chemical, biochemical or biological process. The modules of the analyzer 100 constitute receptacle-receiving structures configured to receive and hold one or more reaction receptacles. The present invention embodies methods and apparatus for transferring reaction receptacles between the various modules of the analyzer 100 and for inserting reaction receptacles into and removing reaction receptacles from the modules.

In one embodiment, an exemplary analyzer in which the present invention may be implemented may include a receptacle input module 102 including structure for receiving and holding one or more empty reaction receptacles prior to the receptacles being used for performing a chemical, biological, or other multi-step analytical process. The receptacle input module 102 may comprise a drawer holding a plurality of receptacles and may include a receptacle feeding apparatus for moving receptacles, e.g., one at a time, into a receptacle pick-up position.

Analyzer 100 may further include load stations 104, 106, 108 configured to receive a reaction receptacle and within which one or more materials may be added to the receptacles, including sample material and various reaction reagents. In an implementation where the analyzer 100 comprises a platform for performing NATs, reaction reagents may comprise target capture reagents, nucleic acid amplification reagents, and nucleic acid detection reagents.

Analyzer 100 may further comprise temperature ramping stations 110 configured to hold one or more reaction receptacles in an environment that is maintained at higher than ambient temperatures so as to raise the temperature of the contents of the receptacles. Analyzer 100 may further include one or more incubators. The illustrated analyzer 100 includes three incubators 112, 114, 116, each of which is configured to receive a plurality of reaction receptacles and maintain the receptacles in an elevated temperature environment.

Also, in an implementation in which the analyzer 100 comprises a platform for performing NATs, the analyzer may include sample-processing modules, such as magnetic separation wash stations 118, 120 adapted to separate or isolate an analyte of interest (e.g., a target nucleic acid) bound to a magnetically-responsive target capture material from the remaining contents of the receptacle. Analyzer 100 may further include chilling modules 122 adapted to receive one or more reaction receptacles and hold the receptacles in a lower than ambient temperature environment so as to reduce the temperature of the contents of the receptacles. Finally, analyzer 100 may include a detector module 124 adapted to receive a reaction receptacle and detect a signal (e.g., an optical signal) emitted by the contents of the reaction receptacle. In one implementation, detector module 124 may comprise a luminometer for detecting luminescent signals emitted by the contents of a receptacle or a fluorometer for detecting fluorescent emissions.

The analyzer 100 further includes a receptacle transfer apparatus, which, in the illustrated embodiment, comprises a receptacle distributor 300, embodying aspects of the present invention. Each of the modules of the analyzer 100 includes a receptacle transfer portal through which receptacles are inserted into or removed from the respective modules. Each module may or may not include an openable door covering its receptacle portal. The receptacle distributor 300 is configured to move receptacles between the various modules and retrieve receptacles from the modules and deposit receptacles into the modules. More specifically, the receptacle distributor 300 includes a receptacle distribution head 312 configured to move in an X direction along a transport track assembly 458, rotate in a theta (Θ) direction, and move receptacles in an R direction into and out of the receptacle distribution head 312 and one of the modules of analyzer 100.

In operation, the receptacle distribution head 312 moves in the X direction along the transport track assembly 458 to a transfer position with respect to one of the modules. The distribution head then rotates in the Θ direction to place the distribution head in a receptacle transfer orientation with respect to the receptacle transfer portal of the module. A receptacle moving mechanism moves in an R direction with respect to the distribution head to move a receptacle from the distribution head into the module or to retrieve a receptacle from the module into the distribution head. As will be described in further detail below, the receptacle distributor further includes means for effecting vertical (Z-axis, normal to the page of FIG. 1) position adjustment of the distribution head to accommodate variations in vertical position of the receptacle transfer portals of the various modules due to, for example, manufacturing and installation tolerances. Also, as will be described in further detail below, the receptacle distributor 300 includes a "self-teaching" system for automatically identifying the correct X, Z, and R transfer positions with respect to the receptacle transfer portal of each module. Finally, the receptacle distributor 300 may include structural elements and associated control logic for opening a door that is covering a receptacle transfer portal before inserting a reaction receptacle into the module or removing the reaction receptacle from the module.

Multiple Receptacle Device

Figure 2:
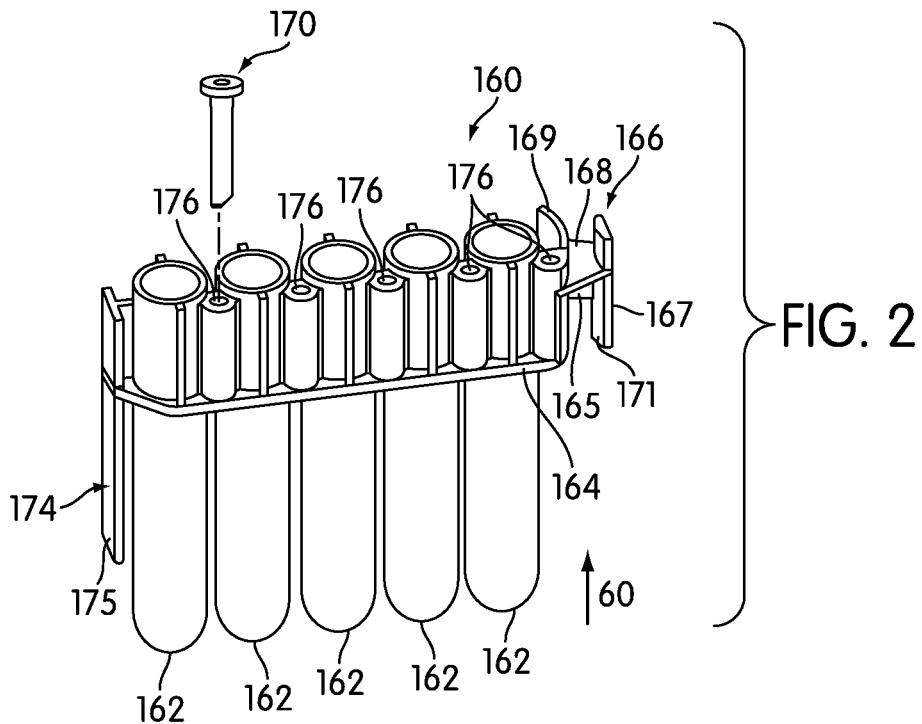
FIG. 2 is a perspective view of a reaction receptacle in the form of a multiple receptacle device employed in combination with an apparatus embodying aspects of the present invention.

As shown in FIG. 2, a reaction receptacle in the form of a multiple receptacle device ("MRD") 160 that can be used in conjunction with the present invention comprises a plurality of individual receptacle vessels 162, five in the illustrated embodiment. Other types of receptacle devices can be used in conjunction with the invention, including devices comprising a single, individual receptacle vessel. In the illustrated embodiment, the receptacle vessels 162 are in the form of cylindrical tubes with open top ends and closed bottom ends and are connected to one another by a connecting rib structure 164 which defines a downwardly facing shoulder extending longitudinally along either side of the MRD 160. In the illustrated embodiment of the MRD 160, all of the receptacle vessels 162 are substantially identical in size and shape. In other embodiments, the MRD may include receptacle vessels of varying size, shape, and type and which can be configured for use with the present invention (e.g., microtiter plates).

In one embodiment, the MRD 160, or other receptacle, is formed from injection molded polypropylene, such as that sold by Montell Polyolefins, of Wilmington, Del., product number PD701NW or by Huntsman, product number P5M6K-048.

An arcuate shield structure 169 is provided at one end of the MRD 160. An MRD manipulating structure 166 extends from the shield structure 169. The manipulating structure is adapted to be engaged by the receptacle distributor 300 for moving the MRD 160 between different locations of the analyzer 100. MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

Figure 3:
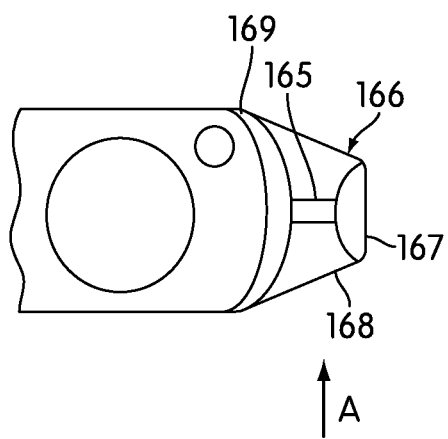
FIG. 3 is an enlarged bottom view of a portion of the multiple receptacle device, viewed in the direction of arrow "60" in FIG. 2.

As shown in FIG. 3, the shield structure 169 and vertical piece 167 have mutually facing convex surfaces. The MRD 160 may be engaged by the distributor 300, by moving an engaging member (e.g., a hook) laterally (in the direction "A" in FIG. 2) into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scannable bar codes, can be placed on the surface 175 to provide identifying and/or instructional information on the MRD 160. The MRD 160 may also include tiplet holding structures 176 adjacent the open mouth of each respective receptacle vessel 162. Each tiplet holding structure 176 provides a cylindrical orifice within which is received a conduit, such as contact-limiting tiplet 170, that is adapted to be placed onto the end of an aspirating tube (no shown). Each holding structure 176 is constructed and arranged to frictionally receive a tiplet 170 in a manner that prevents the tiplet 170 from falling out of the holding structure 176 when the MRD 160 is inverted, but permits the tiplet 170 to be removed from the holding structure 176 when engaged by a pipette. Further details regarding this embodiment of the MRD 160 may be found in U.S. Pat. No. 6,086,827.

Receptacle Distributor

Figure 4:
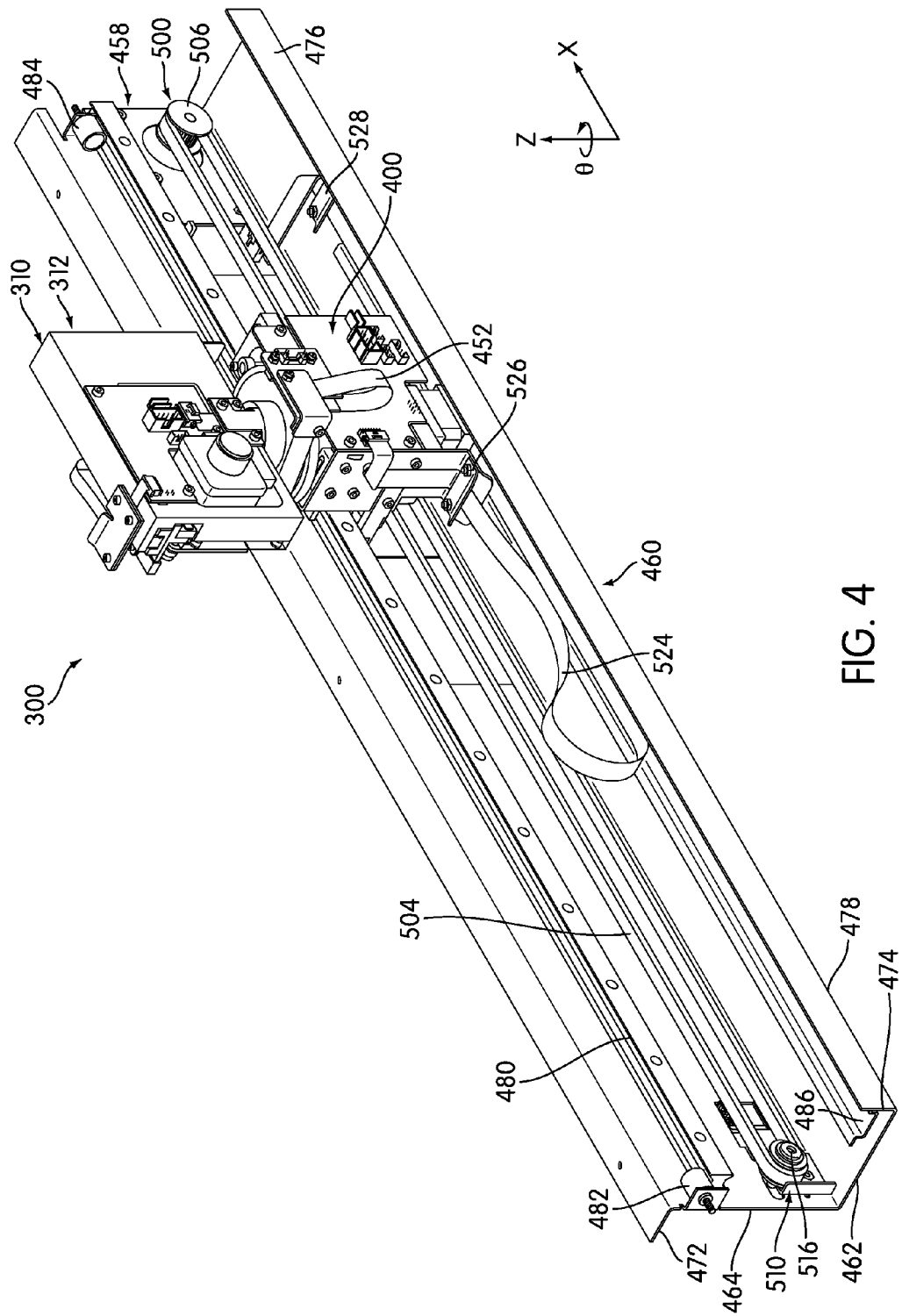
FIG. 4 is a perspective view of a receptacle transfer apparatus in the form of a receptacle distributor embodying aspects of the present invention.
Figure 5:
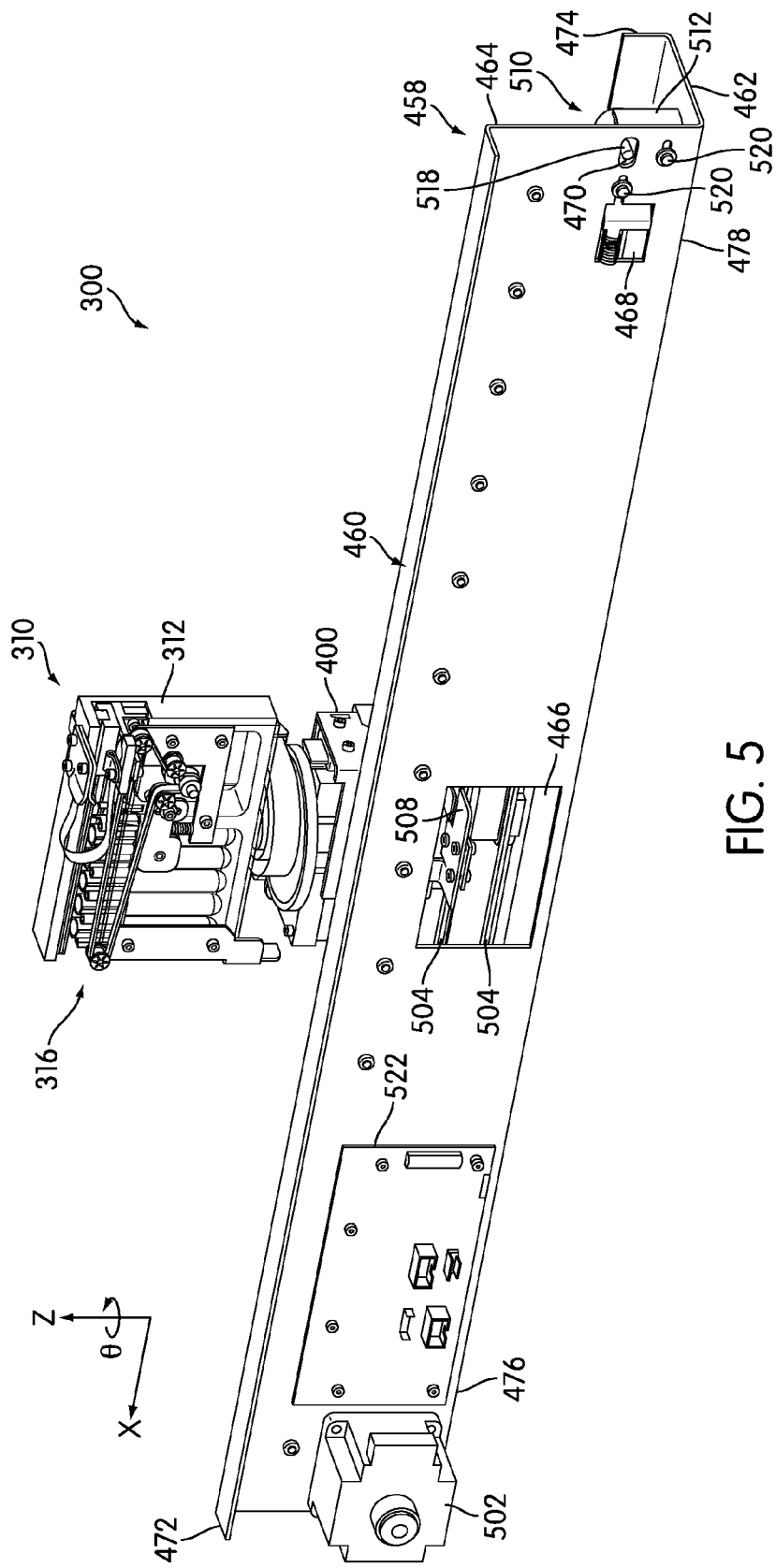
FIG. 5 is a perspective view of an opposite side of the receptacle distributor from that shown in FIG. 4.
Figure 6:
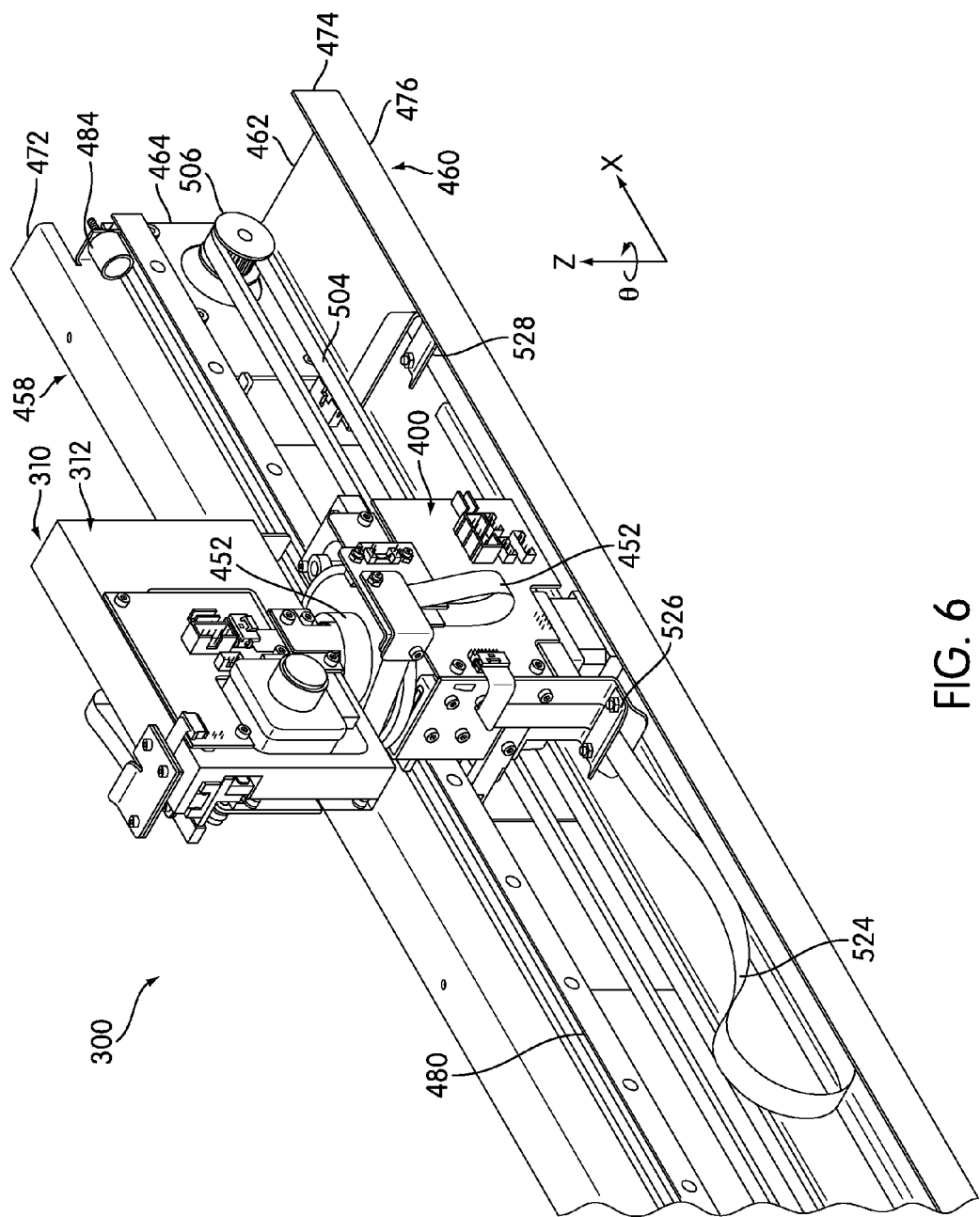
FIG. 6 is an enlarged partial perspective view of the receptacle carrier assembly of the receptacle distributor.

As shown in FIGS. 4-6, a receptacle transfer apparatus in the form of a receptacle distributor 300 comprises a receptacle carrier assembly 310 which translates along a transport track assembly 458 in an "X" direction" under the power of an X-translation system (described below). The receptacle carrier assembly 310 includes a receptacle distribution head 312 configured to carry a reaction receptacle, such as an MRD 160, supported on a carrier assembly carriage 400 constructed and arranged to effect Z-axis translation and Θ rotation of the distribution head 312 as will be described below. In the illustrated embodiment, the track assembly 458 is linear (i.e., straight) and substantially horizontal, but it can be appreciated that aspects of the present invention can be incorporated in, and the scope of the invention encompasses, a receptacle distributor having a track assembly that is non-linear (i.e., at least partially curved) and/or non-horizontal (i.e., at least a portion of the track assembly is inclined or vertical).

In the illustrated embodiment, track assembly 458 comprises a generally "L" shaped channel 460 comprising a base portion 462—oriented substantially horizontally in the illustrated embodiment—and an upright backing 464 extending in an upright manner—oriented substantially vertically in the illustrated embodiment—from one edge of the horizontal base 462. A stiffening flange 474 extends upright from an edge of the base portion 462 opposite the upright backing 464, and a stiffening flange 472 extends laterally from an upper edge of the upright backing 464. A guide rail 480 is mounted to the upright backing 464 and extends in a parallel orientation with respect to the base portion 462. A cable guide track 486 is mounted to the base portion 462.

An X-translation system 500 comprises a drive, or transmission, belt 504 trained over a driven pulley 506 disposed on one side of the upright backing 464 at a distal end 476 of the channel 460 and over an idler pulley 516 disposed on the same side of the upright backing 464 at a proximal end 478 of the channel 460. Driven pulley 506 is operatively coupled to a carrier translation motor 502 mounted to an opposite side of the upright backing 464 (See FIG. 5). Carrier translation motor 502 is preferably a stepper motor with an optical encoder attached to the drive shaft coupled to the driven pulley 506. A suitable motor includes Nanotec model no. ST5918L6404-KSTR-E1, and a suitable encoder includes HEDSS model no. HKT2204-702C-200B-5E. Drive belt 504 is preferably a Kevlar belt with a 5 mm module (T5) cut to length.

As shown in FIG. 5, the drive belt 504 is attached to the carrier assembly 310 by a bracket 508 which fixes the belt 504 to one side of the carriage 400. An access opening 466 in the upright backing 464 provides access to the bracket 508 and facilitates attachment of the carrier assembly 310 to the drive belt 504.

Figure 7:
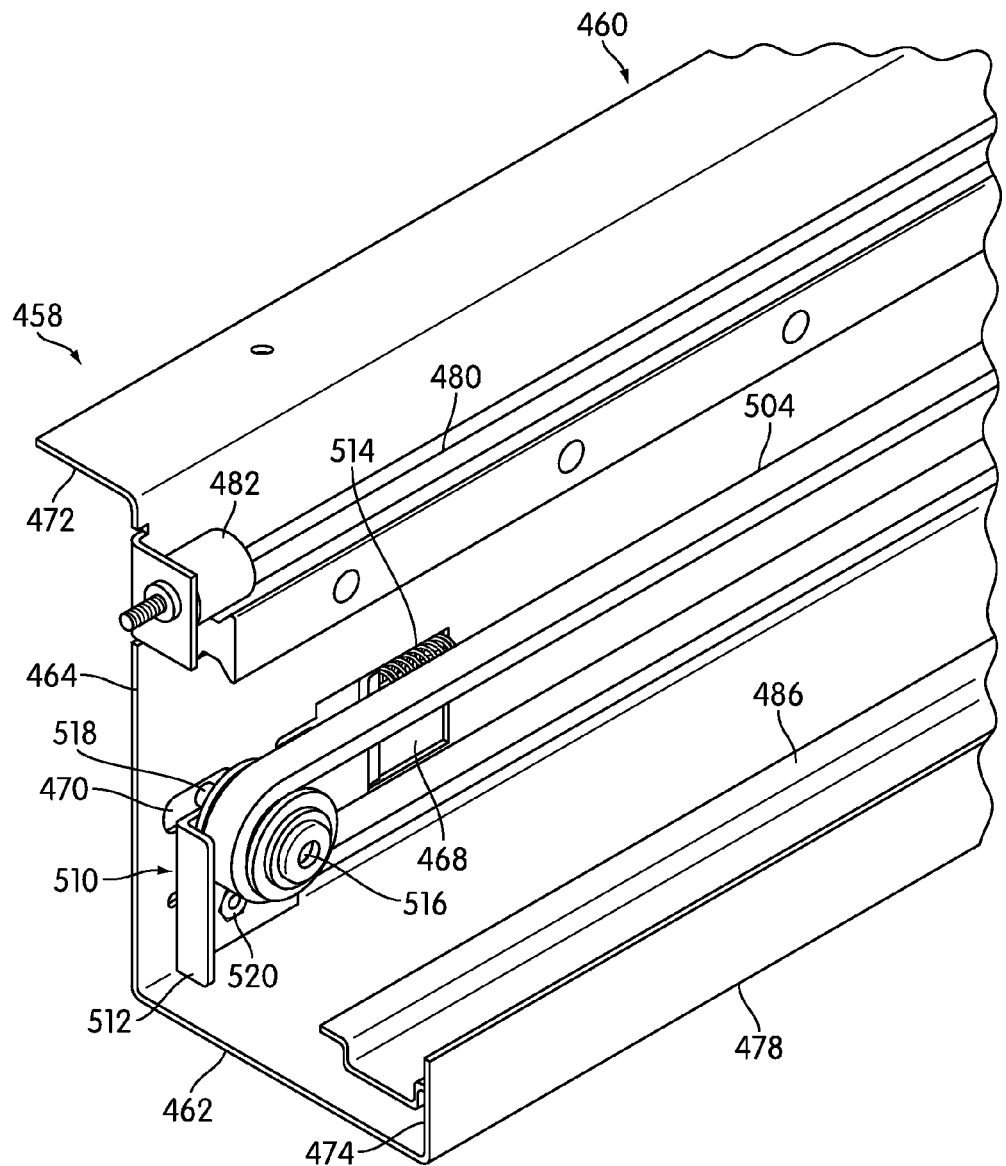
FIG. 7 is an enlarged partial perspective view of a proximal end of a track assembly of the receptacle distributor showing a belt tensioner with pulley and spring.

Referring to FIG. 7, which shows a partial perspective view of the proximal end 478 of track assembly 458, the drive belt 504 is preferably equipped with a belt tensioner 510. Belt tensioner 510 comprises a sliding pulley mount 512, on which is mounted the idler pulley 516, and a spring 514. Spring 514 is disposed within an opening 468 formed in the upright backing 464 of the channel 460 and is compressed between an edge of the opening 468 and a portion of the sliding pulley mount 512 disposed within or adjacent to the opening 468. Sliding pulley mount 512 includes a transverse pin 518 extending into a longitudinally-extending slot 470 formed in the upright backing 464. Screws 520 extend through the sliding pulley mount 468 and into slotted openings formed in the upright backing 464. During assembly of the receptacle distributor 300, the drive belt 504 is placed on the driven pulley 506 of the carrier translation motor 502 at the distal end 476 of the transport track assembly 458. The sliding pulley mount 512 and the idler pulley 516 are pushed against the spring 514 toward the driven pulley 506 (as far as the length of slot 470 within which pin 518 extends will permit), and the sliding pulley mount 512 is fixed with screws 520 to permit the drive belt 504 to be placed onto the idler pulley 516 at the proximal end 478 of the transport track assembly 458. The screws 520 of the belt tensioner 510 are then loosened, and the drive belt 504 tension is maintained by the spring 514, which urges the sliding pulley mount 512 and pulley 516 in a direction away from the driven pulley 506. The location of the pulley 516 is then fixed by screws 520 after the spring 514 effects proper tension on the drive belt 504.

The distribution head 312 of the carrier assembly 310 is carried along the transport track assembly 458 by the carrier assembly carriage 400. The carrier assembly carriage 400 engages the guide rail 480, and translates along the transport track assembly 458. Rubber bumpers 482, 484 may be provided at opposite ends of the guide rail 480 to absorb contact by the carriage 400. Movement of the carrier assembly carriage 400 along the guide rail 480 is effected by the drive belt 504. When the carrier translation motor 502 rotates the driven pulley in a counter-clockwise fashion, the carrier assembly 310 is moved in a first X direction (to the left in the illustrated embodiment) towards the proximal end 478 of transport track assembly 458. Similarly, when the carrier translation motor 502 rotates driven pulley 506 in a clockwise fashion, the carrier assembly 310 translates in a second X direction (to the right in the illustrated embodiment) towards the distal end 476 of transport track 458 assembly.

In one embodiment, the carrier assembly 310 has a linear travel of 750 mm. The diameter of the driven pulley 506 is preferably 21.45 mm, providing a resolution of 0.337 mm/step of the carrier translation motor 502 in full step mode. The encoder of motor 502 offers a resolution of 200 counts/revolution (A-B signals) resulting in a quadrupled resolution of 800 counts/revolution.

Figure 8:
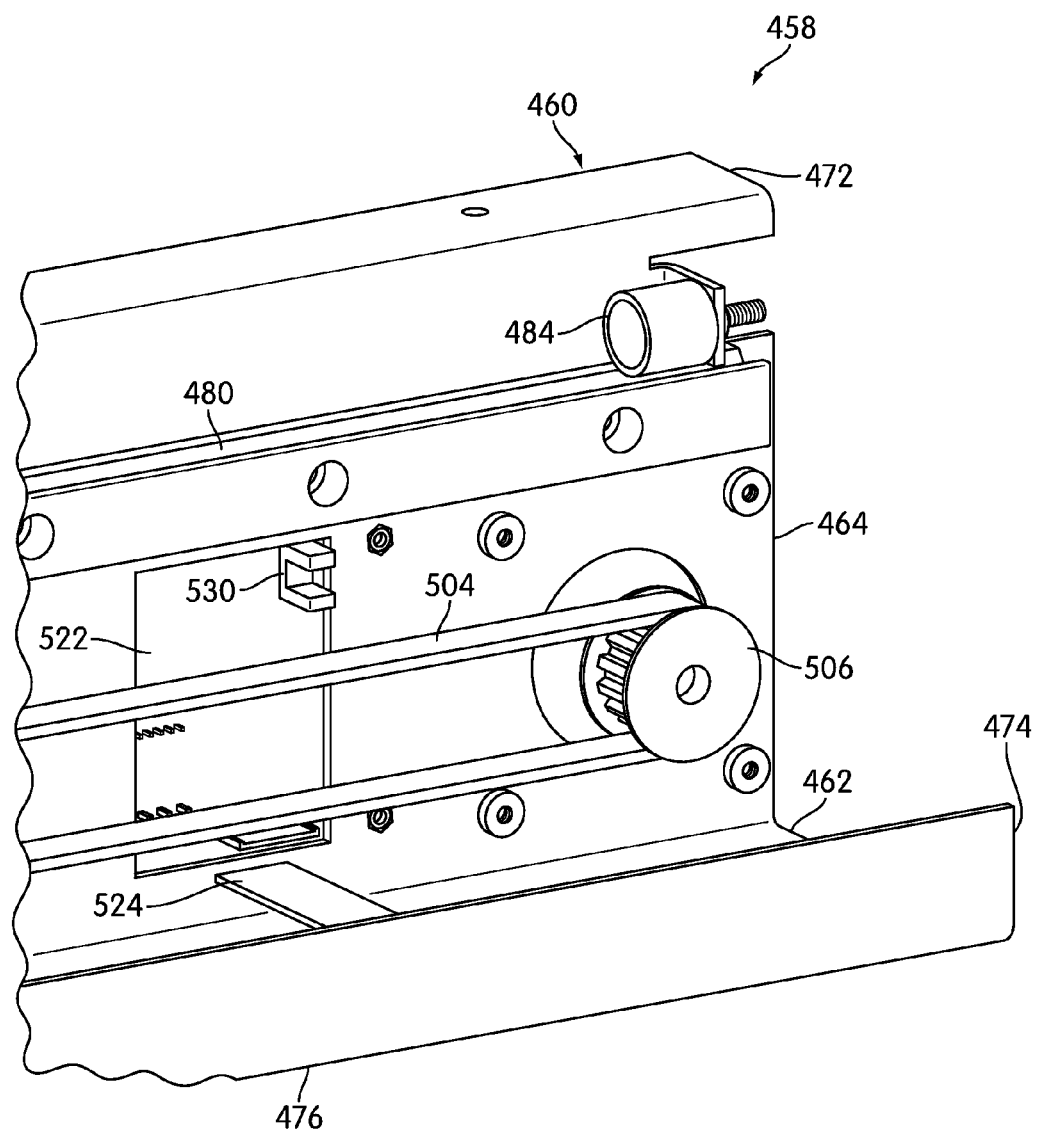
FIG. 8 is an enlarged partial perspective view of a distal end of the track assembly of the receptacle distributor showing a home position sensor and carrier translation belt drive wheel.

As shown in FIGS. 5 and 8, which shows a partial perspective view of the distal end 476 of track assembly 458, an X-drive printed circuit board ("PCB") 522 for the carrier translation motor 502 is mounted on the upright backing 464 of the channel 460 adjacent to the carrier translation motor 502. X-drive PCB 522 is electronically coupled to the carrier assembly carriage 400 by a flexible cable 524. Cable guide 486 guides the flexible cable 524 as the carrier assembly carriage 400 translates to various positions along the transport track assembly 458. Strain reliefs 526, 528 secure the flexible cable 524 to the carrier assembly carriage 400 and to the transport track assembly 458, respectively.

As shown in FIG. 8, a "home" sensor 530, mounted on the X-drive PCB 522, detects when the carrier assembly 310 is at the distal end 476 of the transport track assembly 458. Sensor 530 is preferably a slotted optical sensor which is "tripped" when a structural element (e.g., a rod or flag) projecting from the carrier assembly carriage 400 disrupts the sensor. A suitable sensor includes OPTEK model no. OPB 900W55.

Figure 10:
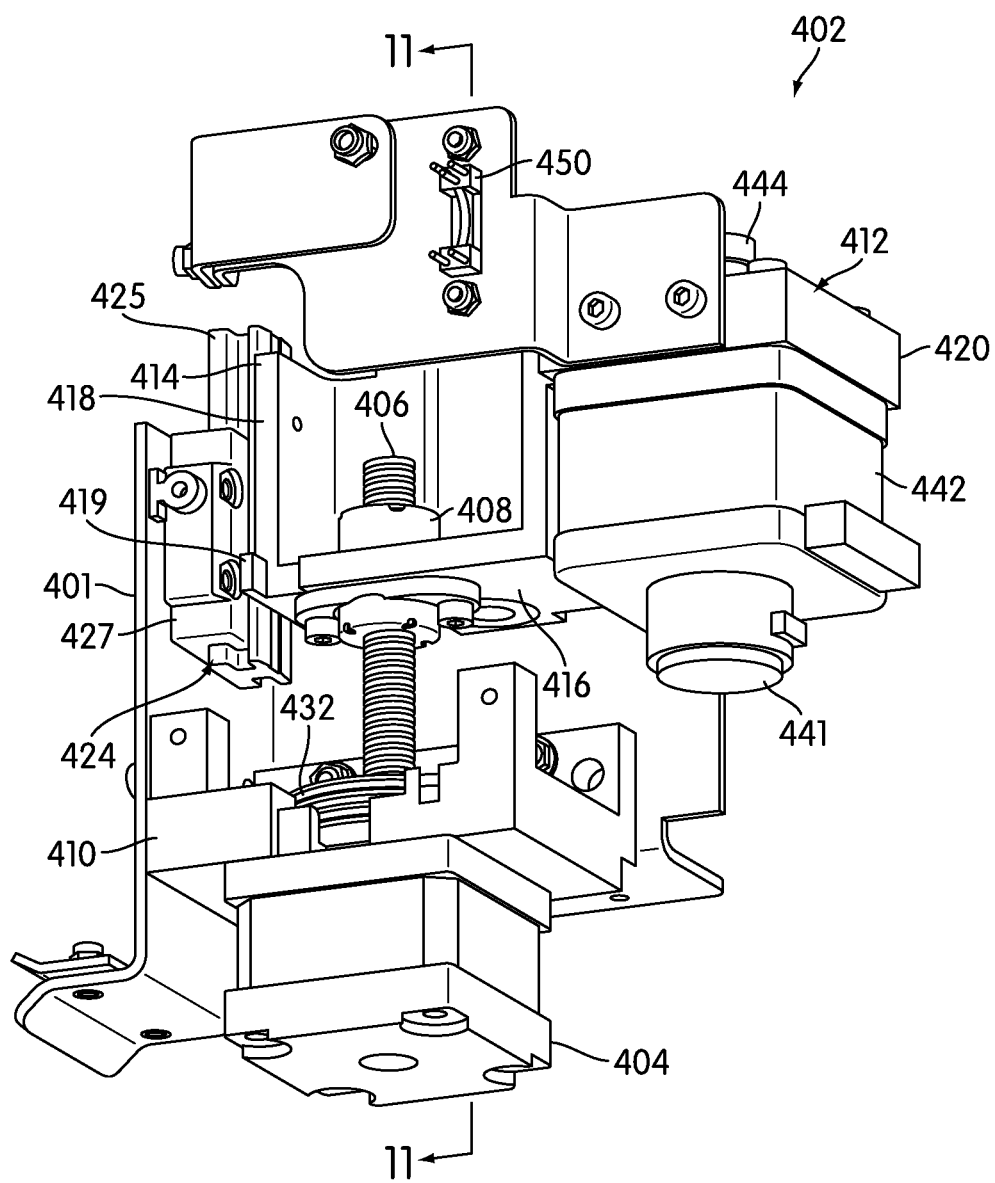
FIG. 10 is a perspective view of a Z-axis drive system of the carrier assembly carriage of the receptacle carrier assembly.
Figure 11:
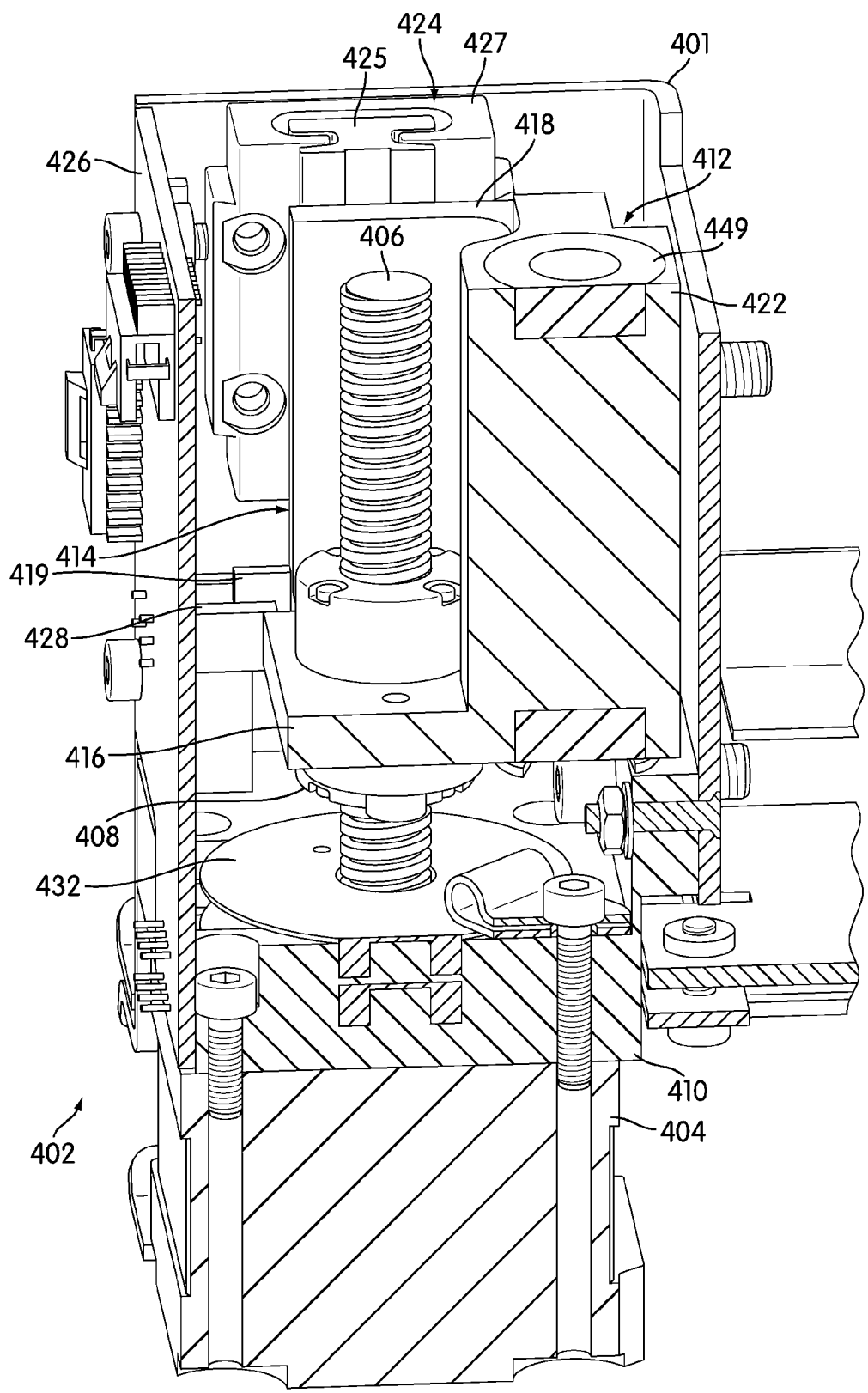
FIG. 11 is a perspective view, partially in cross-section along the line 11-11, of the Z-axis drive system of FIG. 10.

While X-axis translation of the carrier assembly 310 and distribution head 312 along the track assembly 458 is effected by the motor 502 and driven pulley 506 rotating the drive belt 504 attached to the carrier assembly carriage 400, transverse, or Z-axis, translation of the distribution head 312 with respect to the track assembly 458 is effected by a Z-axis drive system 402 housed within the carrier assembly carriage 400. Referring to FIGS. 10 and 11, which show the Z-axis drive system 402 that is housed in the carrier assembly carriage 400, the Z-axis drive system 402 includes a Z-drive stepper motor 404, mounted to a motor mount 410, and an elevation block 412 which is operatively coupled to the motor 404 by means of a ball screw 406 engaged with a ball nut 408 that is attached to a lower panel 416 of a box chamber portion 418 of the elevation block 412. A suitable motor includes Nanotec model no. ST4118M1404-B. The distribution head 312 is supported on the elevation block 412 and translates transversely up or down under the power of the motor 404 via rotation of the ball screw 406 engaged with the ball nut 408. The elevation block 412 is supported for transverse (vertical in the illustrated embodiment) movement with respect to the track assembly 458 by a linear guide 424 comprising a guide rail 425, attached to a vertical outer wall 418 of the box chamber portion 414 of the elevation block 412, and a linear bearing 427 (e.g., an IGUS linear guide bearing), attached to a portion of a carriage housing wall 401 of the carriage 400.

As shown in FIG. 11, a Z "home" position sensor 428 is mounted to a Z-drive PCB 426 and signals the lower most position of the elevation block 412. The Z-home position sensor 428 is preferably a slotted optical sensor which is "tripped" when a home flag 419 projecting from the box chamber portion 414 of the elevation block 412 disrupts the sensor 428. A suitable sensor includes a Sharp model no. GP1S94. An angular encoder is comprised of two slotted optical sensors (not shown) on the Z-drive printed circuit board 426 together with a slotted disk 432 which rotates with the shaft of the motor. Suitable sensor include Sharp model no. GP1S94. The theoretical resolution of the encoder is preferably 0.04 mm.

Figure 9:
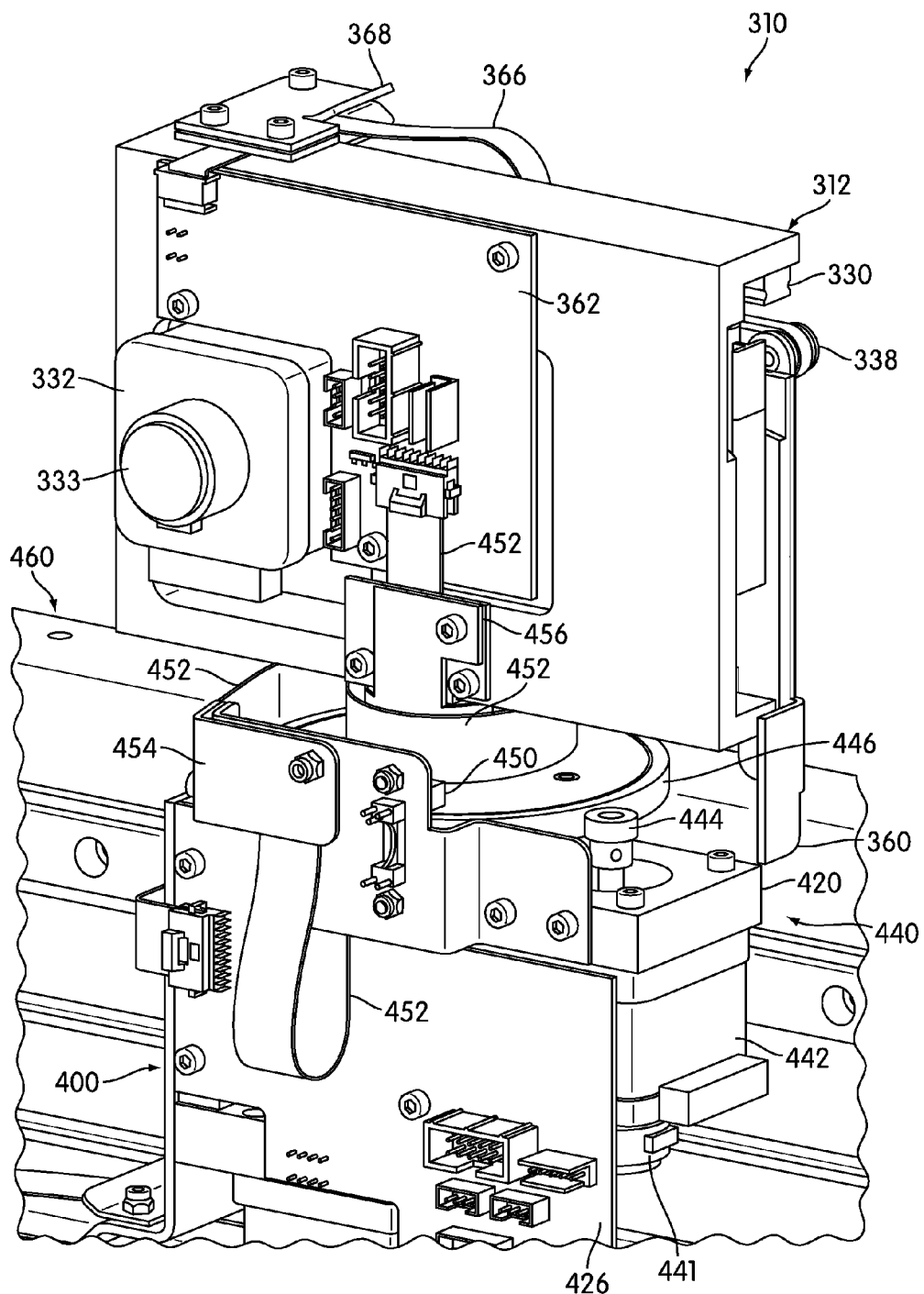
FIG. 9 is an enlarged partial perspective view of the receptacle carrier assembly showing a receptacle distribution head and a portion of a carrier assembly carriage.
Figure 12:
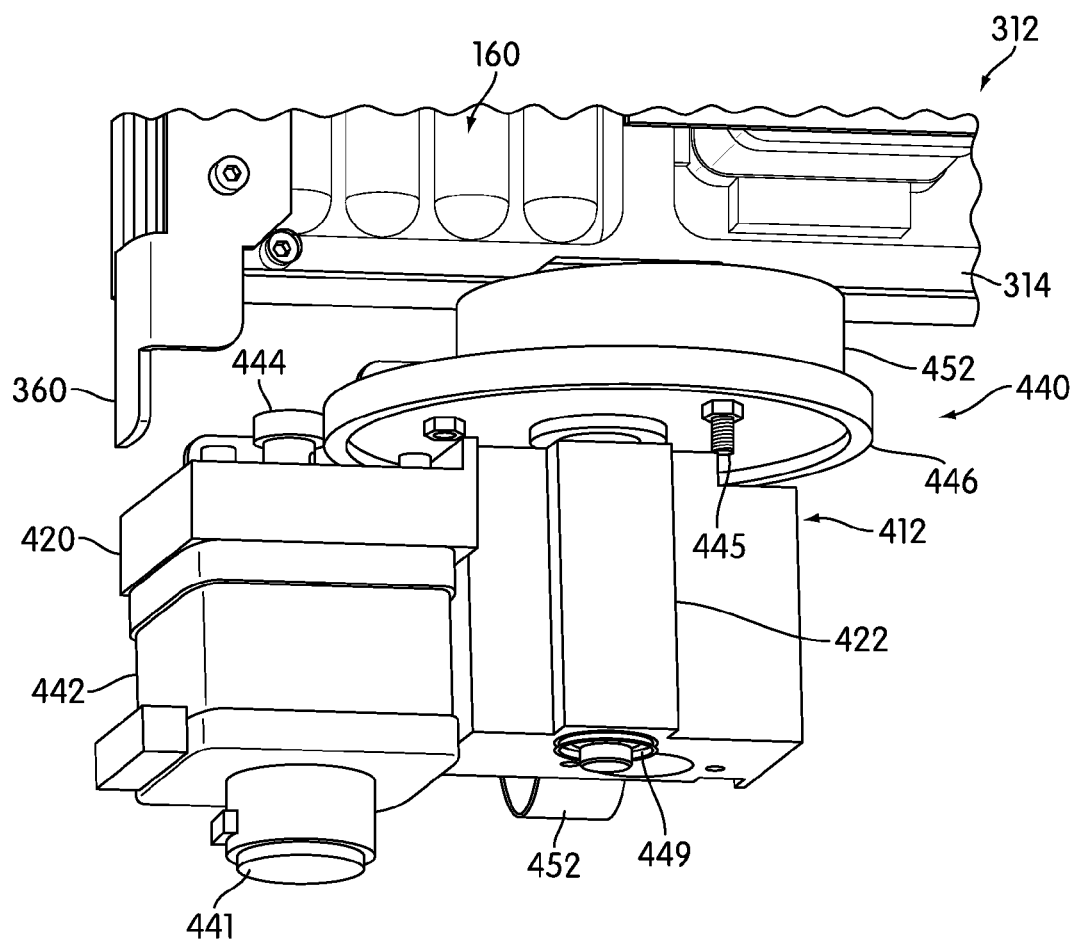
FIG. 12 is a partial perspective view of a carrier rotation system (θ drive system) of the carrier assembly carriage of the receptacle carrier assembly.
Figure 13:
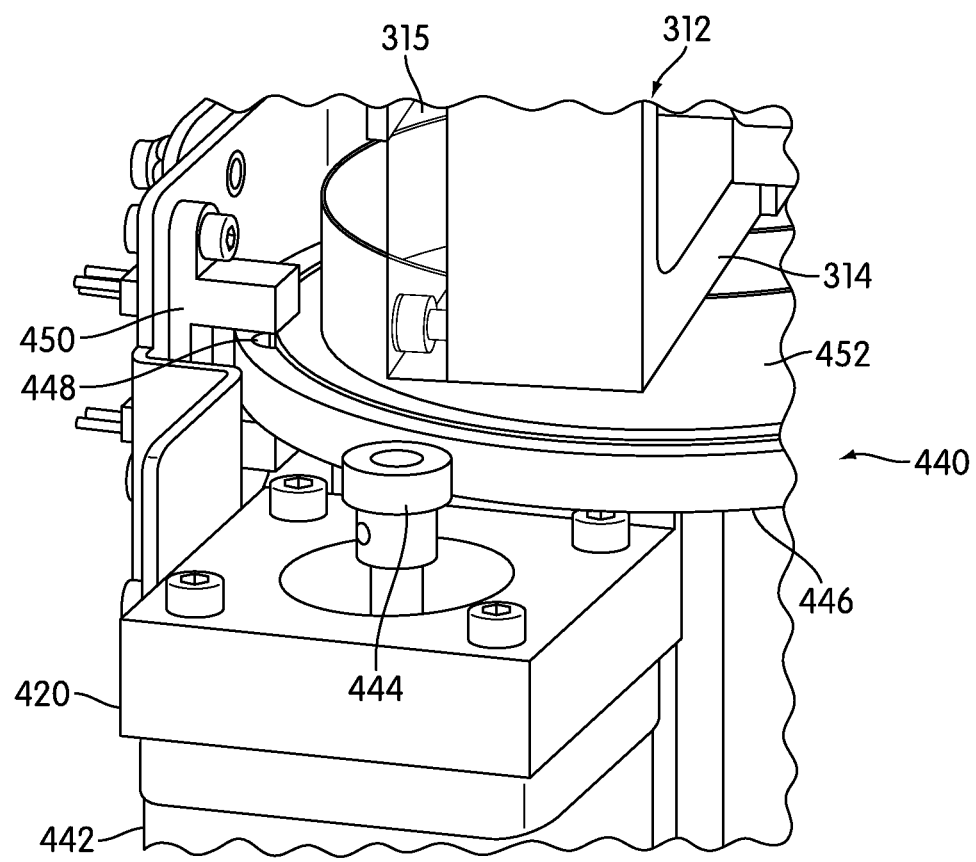
FIG. 13 is an enlarged partial perspective view of a portion of the carrier rotation system.

Rotation of the distribution head 312 is effected by a Θ drive system that is also located within the carrier assembly carriage 400 and indicated generally by reference number 440 in FIGS. 9, 12, and 13. The Θ drive system comprises carrier rotation motor 442 mounted on a motor mount portion 420 of the elevation block 412, a platform gear 446 on which the distribution head 312 is carried and which is rotatably mounted on a shaft (not shown) supported within a bearing 449 (see also FIG. 11) pressed into a bearing block portion 422 of the elevation block 412, and drive gear 444 mounted on the output shaft of motor 442. Bearing 449 and the shaft supported therein define an axis of rotation of the distribution head 312 corresponding to the longitudinal axis of the bearing 449. A suitable motor includes Nanotec model no. ST4118S1404-KSTR-E1. A rotational encoder 441 is coupled to the motor 442. A suitable encoder includes HEDSS model no. HKT2204-702C-200B-5E. Drive gear 444 is operatively engaged with platform gear 446, for example, by mating gear teeth. As can be appreciated from FIGS. 12 and 13, rotation of the drive gear 444 by motor 442 causes a corresponding rotation of platform gear 446, which in turn rotates the distribution head 312 in the Θ direction.

In the illustrated embodiment, track assembly 458 is substantially horizontal, and the axis of rotation defined by the longitudinal axis of the bearing 449 is substantially vertical and normal to the track assembly 458. It can be appreciated, however, that aspects of the present invention can be incorporated in, and the scope of the invention encompasses, a distribution head that is rotatable on an axis of rotation that is not necessarily vertical or normal to the track assembly 458.

Distribution head 312 is operatively coupled for electronic communication with the carriage 400 by flexible cable 452, which is connected at one end to z-drive PCB 426 attached to the carriage 400 and at its opposite end to a hook extension PCB 362 attached to the distribution head 312 (see FIG. 9). Strain reliefs 454 and 456 secure the flexible cable 452 to the carrier assembly carriage 400 and to the distribution head 312, respectively. As shown in FIGS. 12 and 13, an intermediate portion of the cable 452 is loosely coiled around the axis of rotation of the platform gear 446 to accommodate rotation of the distribution head 312

As shown in FIGS. 9 and 13, the rotational position of the distribution head 312 is determined by means of a Θ home sensor 450, preferably a slotted optical sensor. A suitable sensor includes OPTEK model no. OPB 900W55. An aperture 448 is formed through the platform gear 446. When the platform gear 446 rotates to the home position, sensor 450 encounters the aperture 448, thereby tripping the sensor 450 (by un-blocking the sensor beam) to indicate the home rotational position of the platform gear 446, and thus the distribution head 312. In one embodiment, the home position of the distributor head 312 corresponds to alignment of the distribution head 312 with the longitudinal (X) axis of the track assembly 458, and is the preferred orientation of the distributor head 312 when the carrier assembly 310 is translating along the track assembly 458.

The distribution head 312 for the receptacle vessels 162 preferably rotates 280° to reach any direction where the receptacle transfer portals of analyzer modules are located on the automated analyzer. The rotation angle of the distribution head is limited to 280° by a mechanical stop, such as the screw 445 protruding through the bottom of gear 446 in FIG. 12 that will hit the block 412 to limit rotation.

The carrier rotation motor 442 is preferably a stepper motor with a rotational encoder 441 attached to the motor shaft. The resolution for the rotational encoder is preferably 200 counts/revolution (A-B signals), resulting in a quadrupled resolution of 800 counts/rev. The gear ratio between platform gear 446 and drive gear 444 is preferably 8 to 1. In full step mode, the angular steps for the drive system Θ are preferably 0.225°. Motor 442 is preferably mounted in slots formed in the motor mount portion 420 of the elevation block 412 and is pushed towards the platform gear 446 during production to avoid slack.

Details of the distribution head 312 are shown in FIGS. 14-18. Distribution head 312 includes a distribution frame 314 that is attached to the platform gear 446 of the theta drive system 440. A side panel 315 is attached to one side of the distribution head frame 314. Side panel 315 may be transparent so that the interior of the distribution head 312 is visible. Distribution head 312 further includes a receptacle hook 318 configured to engage the manipulating structure 166 of an MRD 160. Devices other than a hook for engaging the receptacle and enabling physical manipulation of the engaged receptacle are encompassed within the scope of the invention.

Figure 14:
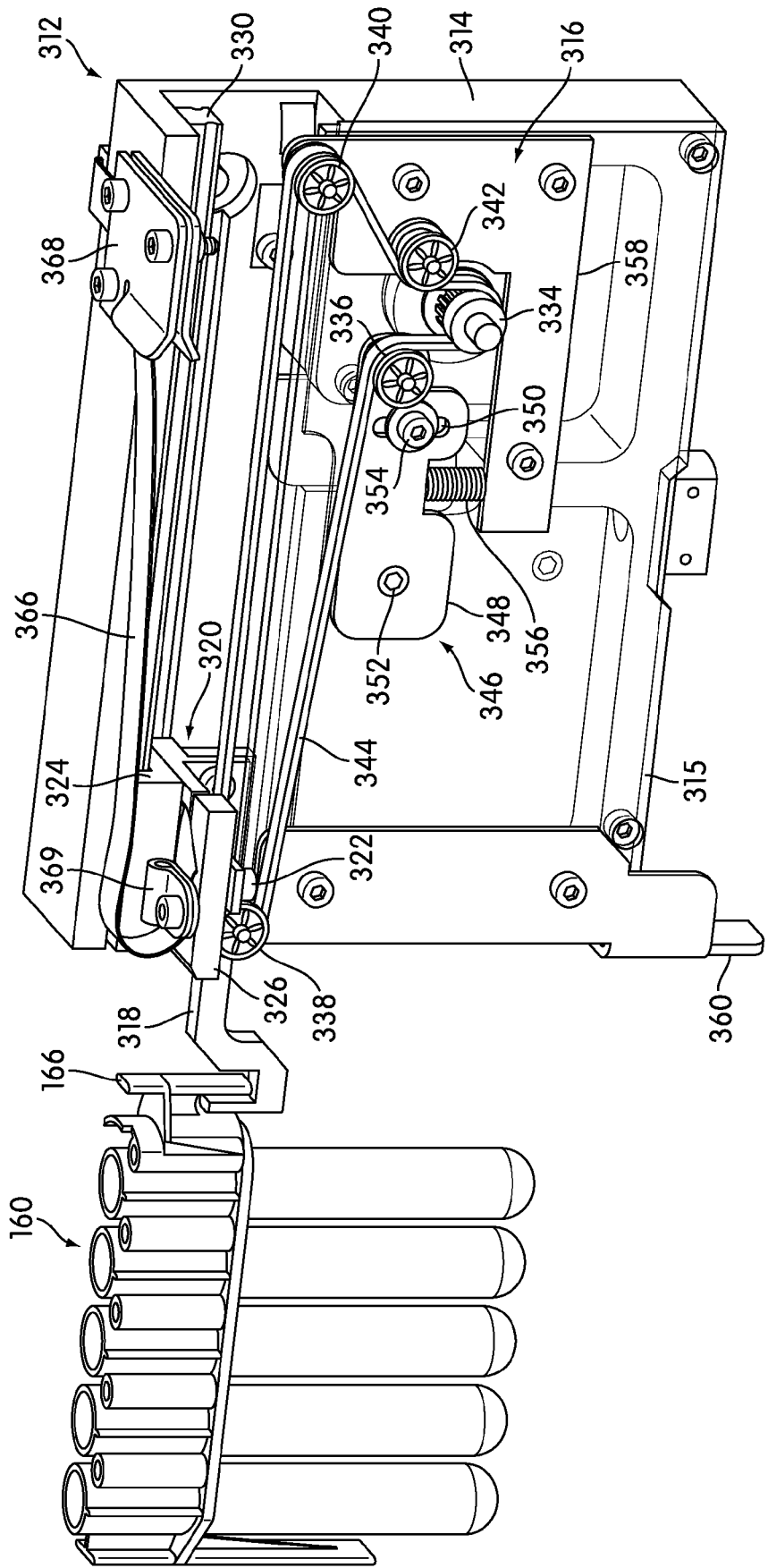
FIG. 14 is a perspective view of the receptacle distribution head and a hook actuator system in an extended position.
Figure 15:
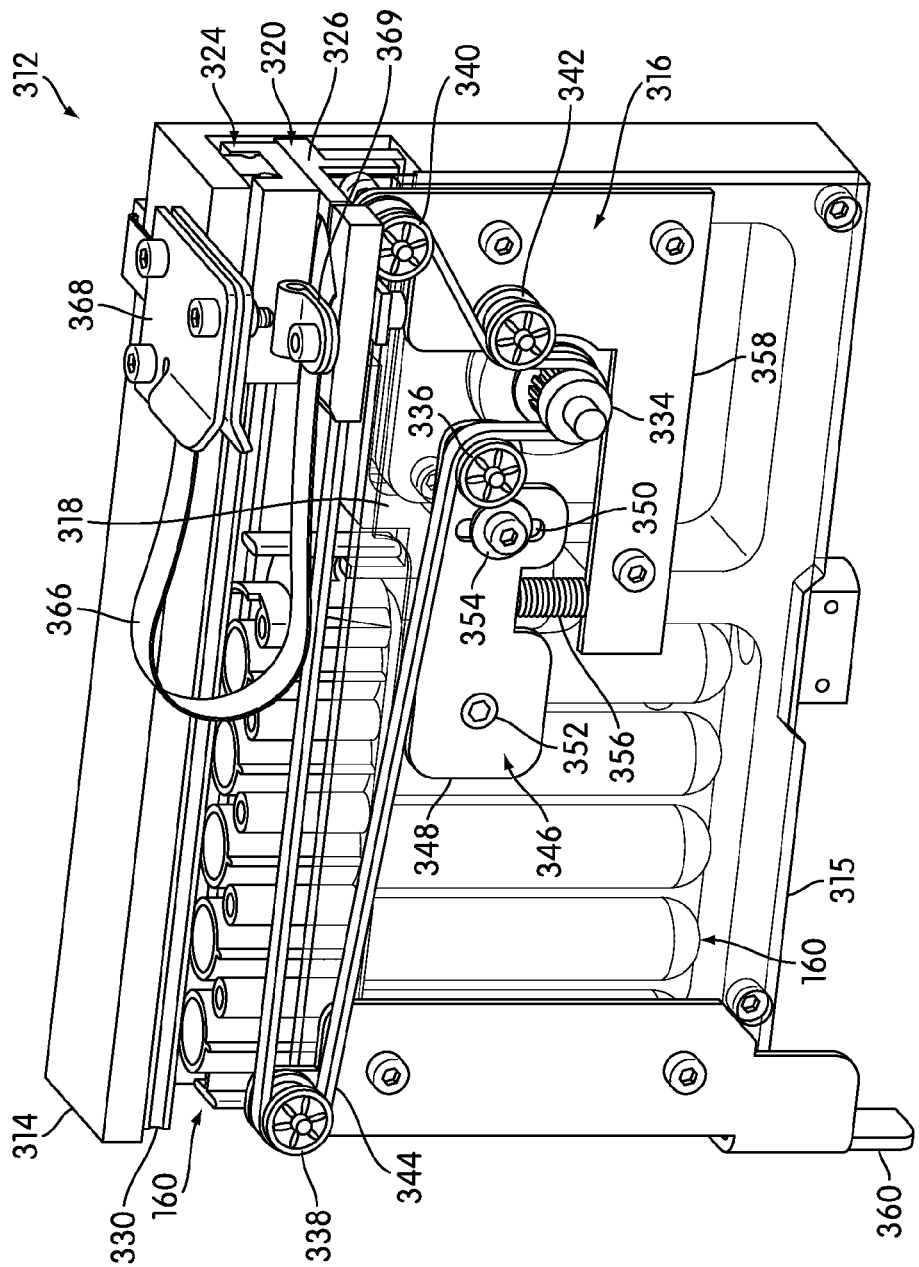
FIG. 15 is a perspective view of the receptacle distribution head and the hook actuator system in a retracted position and a multiple receptacle device inside the distribution head.
Figure 16:
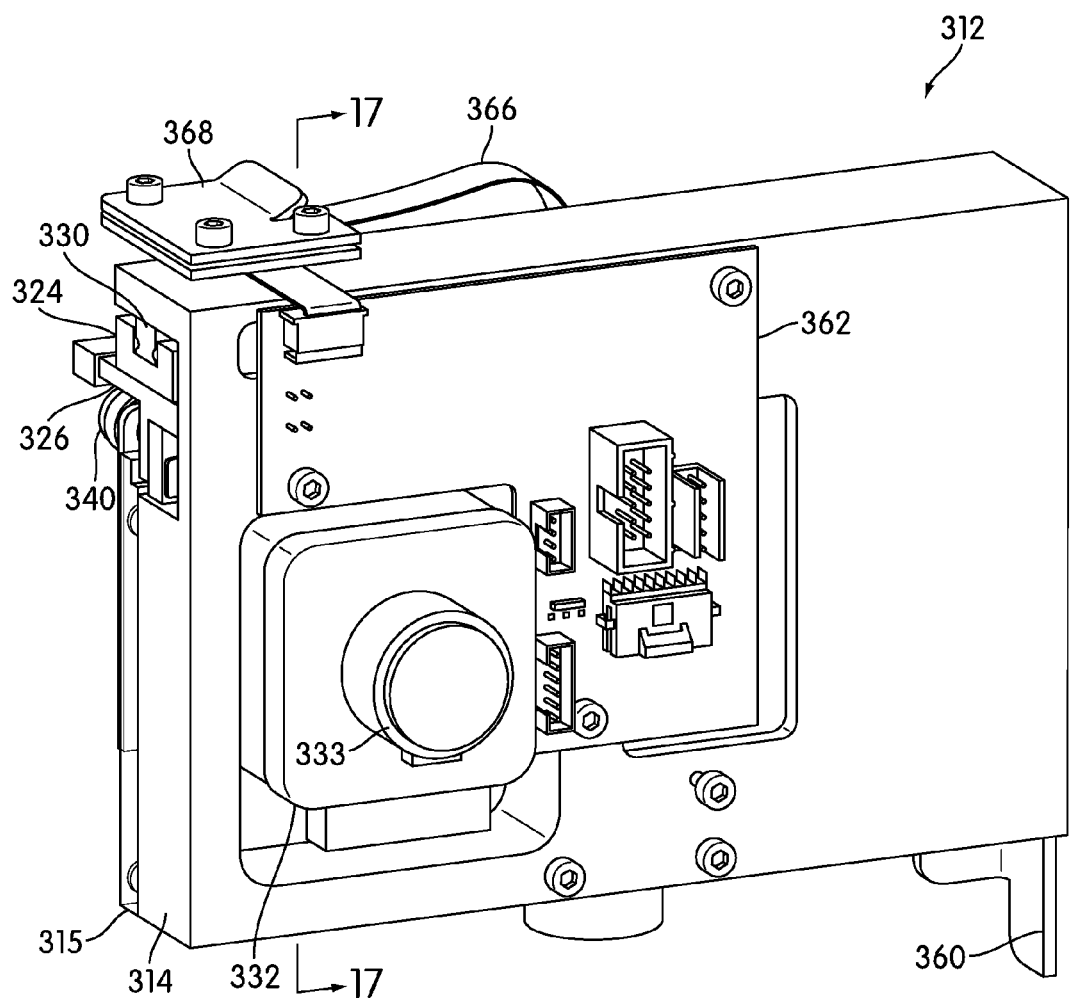
FIG. 16 is a perspective view of the receptacle distribution head from a side opposite that shown in FIGS. 14 and 15.

A hook actuator system 316 effects linear translation (in the R direction) of the receptacle hook 318 between an extended position, as shown in FIG. 14, and a retracted position, as shown in FIG. 15. The hook actuator system 316 includes a hook carriage 320 to which the receptacle hook 318 is attached. A drive belt 344 is attached to the hook carriage 320 by a screw and bracket indicated at 322. Drive belt 344 is carried on a drive wheel 334 and idler wheels 336, 338, 340, 342. Idler wheels 340 and 342 are attached to a fixed idler wheel bracket 358, and idler wheel 338 is attached to an upper portion of a door engagement bracket 360 exterior to panel 315.

Door engagement bracket 360 may be provided for opening a door covering a receptacle transfer portal of a module of the analyzer 100. The door, which may be a pivoting, sliding, or rotating door, will include an arm or other projection depending from a portion of the door. The distribution head 312 is positioned with the lower end of the door engagement bracket 360 in contact with the arm, and a slight X and/or Θ movement of the distribution head 312 is effected to move the door from a closed to an open position. The door is preferably spring-biased in a closed position, so that that when the arm is released from contact with the door engagement bracket 360, the door will spring back to the closed position.

Drive wheel 334 is attached to an output shaft of drive motor 332, which is preferably a stepper motor. A suitable motor includes Nanotec model no. ST4118M1404-B. A rotational encoder 333 is attached to the drive motor 332. A suitable encoder includes HEDSS model no. HKT2204-702C-200B-5E. Drive wheel 334 preferably has a diameter of 9.55 mm resulting in a resolution of 0.15 mm per full motor step. The encoder 333 had a resolution of 200 counts/revolution (A-B signals) resulting in a quadrupled resolution of 800 counts/revolution.

The hook actuator system 316 preferably includes a belt tensioner 346 for maintaining proper tension in the belt 344. Belt tensioner 346 includes a pivoting idler wheel bracket 348 to which idler wheel 336 is attached and which is pivotally attached to the side panel 315 by a pivot screw 352. A slot 350 is formed in an end of the pivoting idler wheel bracket 348, and a position lock screw 354 extends through the slot 350 into the side panel 315. A spring 356 is disposed between a portion of the pivoting idler wheel bracket 348 and the fixed idler wheel bracket 358. Tension in the belt 344 can be adjusted by loosening the position lock screw 354, thereby allowing the spring 356 to pivot the pivoting idler wheel bracket 348 and thus urge the idler wheel 336 upwardly to create the proper tension in the drive belt 344. When proper tension is achieved in the drive belt 344, the position lock screw 354 can thereafter be retightened.

The hook carriage 320 includes a rail channel 324 that translates along a hook carriage guide rail 330 attached to an upper portion of the distribution head frame 314. The receptacle hook 318 is attached to an insulation mount 326 disposed between the rail channel 324 and the hook 318 to electrically isolate the hook 318 from the distribution head 312 to facilitate capacitive sensing of contact by the hook 318 with another structural element of the analyzer 100, as will be described below.

Figure 18:
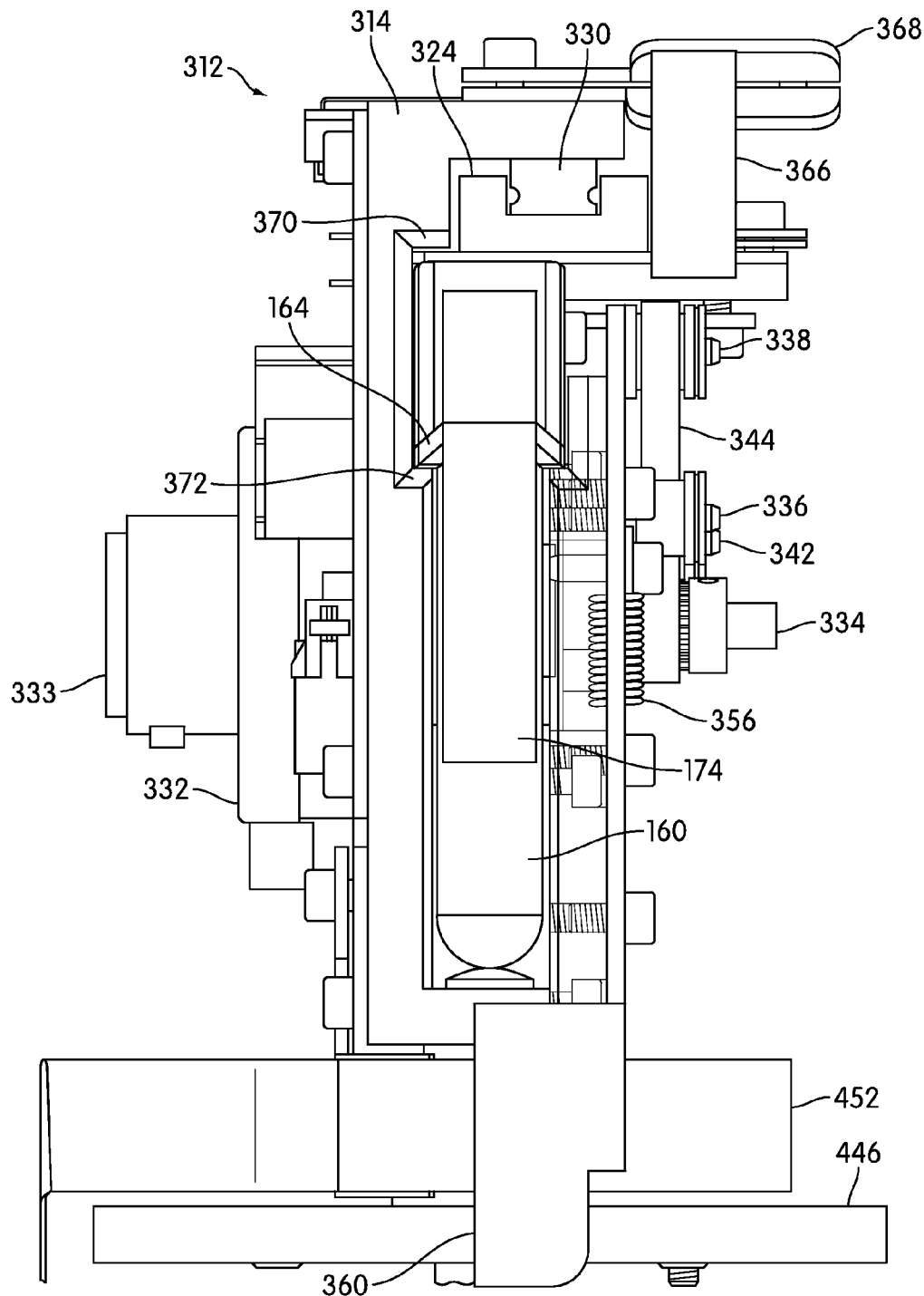
FIG. 18 is an end view of the receptacle distribution head.

As shown in FIG. 18, the distribution head 312 preferably includes an MRD support ledge 372 for supporting the shoulder defined by connecting structure 164 of the MRD 160. Also, an MRD guide 370 is provided in the interior of the distribution head frame 314 to prevent the MRD from lifting up inside the distribution head 312.

Figure 17:
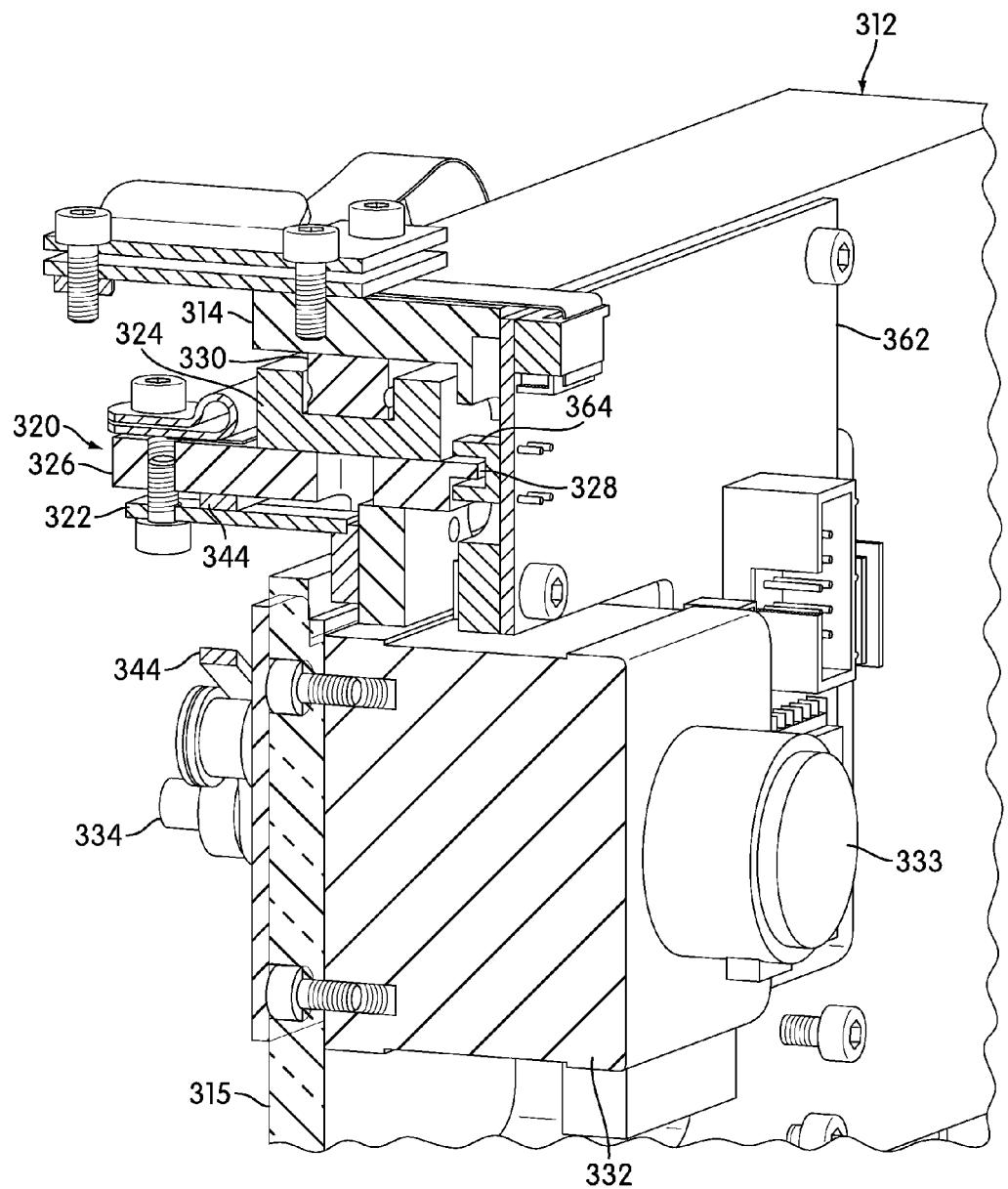
FIG. 17 is a partial cross-sectional perspective view of the distribution head along the line 17-17 in FIG. 16.

A hook extension PCB 362 is attached to one side of the distribution head 312 (see FIG. 17). A hook home sensor 364, preferably a slotted optical sensor, is attached to the hook extension PCB 362. A suitable sensor includes Sharp model no. GP 1S94. The hook sensor 364 indicates when the hook is in the retracted, or "home," position when a sensor flag 328 extending from the insulation mount 326 extends into the slotted optical sensor 364. The receptacle hook 318 and hook carriage 320 are operatively coupled for electronic communication with the remainder of the distribution head 312 by means of a flexible cable 366 attached at one end to the hook carriage 320 and at an opposite end to the hook extension PCB 362. Strain reliefs 368 and 369 may be provided for securing the flexible cable 366 to the distribution head frame 314 and the hook carriage 320, respectively.

The automatic analyzer of the present invention includes a transfer position locating system and method adapted to automatically determine, for each receptacle-receiving structure comprising a module of the analyzer 100, the location of the transfer position of the distribution head 312 with respect to the receptacle-transfer portal to enable the distribution head 312 to transfer a receptacle or group of receptacles, such as MRD 160, between the distribution head and the module.

In one embodiment, the transfer position locating method includes the steps of moving the distribution head 312 along the transport track 458 to an approximate location of one of the receptacle-receiving structures (e.g., analyzer modules) and stopping the distribution head 312 at the approximate location and moving the distribution head 312 (or a portion thereof, e.g., hook 318) with respect to the receptacle-receiving structure in two or more directions until a position locator element associated with the distribution head 312 engages a position locator element associated with the receptacle-receiving structure. Engagement of the position locator element associated with the distribution head 312 with the position locator element associated with the receptacle-receiving structure indicates that the distribution head 312 is in a transfer position with respect to the receptacle-receiving structure (or, alternatively, that the distribution head is at a known distance and direction from the transfer position) to enable the distribution head 312 to transfer a receptacle between the distribution head 312 and the receptacle-receiving structure. The transfer position coordinates for that receptacle-receiving structure are stored, and the steps are repeated for each of the receptacle-receiving structures. The distribution head 312 can later be positioned with respect to each receptacle-receiving structure to enable the distribution head 312 to transfer a receptacle between the distribution head and the receptacle-receiving structure by retrieving the stored transfer position coordinates associated with a receptacle-receiving structure and moving the distribution head to the retrieved transfer position.

The position locator element associated with the distribution head 312 of the present invention is preferably in the form of the hook 318, which is coupled to a capacitive detection system for detecting that the hook 318 has contacted another structure. The position locator element associated with the receptacle-receiving structure, or analyzer module, is preferably in the form of a projection (e.g., a metal pin) extending from the module at a known position with respect to the transfer position for that module. Other position locator elements may comprise hall effect sensors or optical sensors (e.g., slotted optical sensors or reflective sensors). Other optically-based position locators include a camera using image processing to find a fiducial. The position locator element may also be located in a known position with respect to an opening arm of a receptacle transfer portal door, so that location of the position locator element of a module also defines a position for the distribution head 312 to enable the door engagement bracket 360 to engage the door opening arm of the module.

Figure 19:
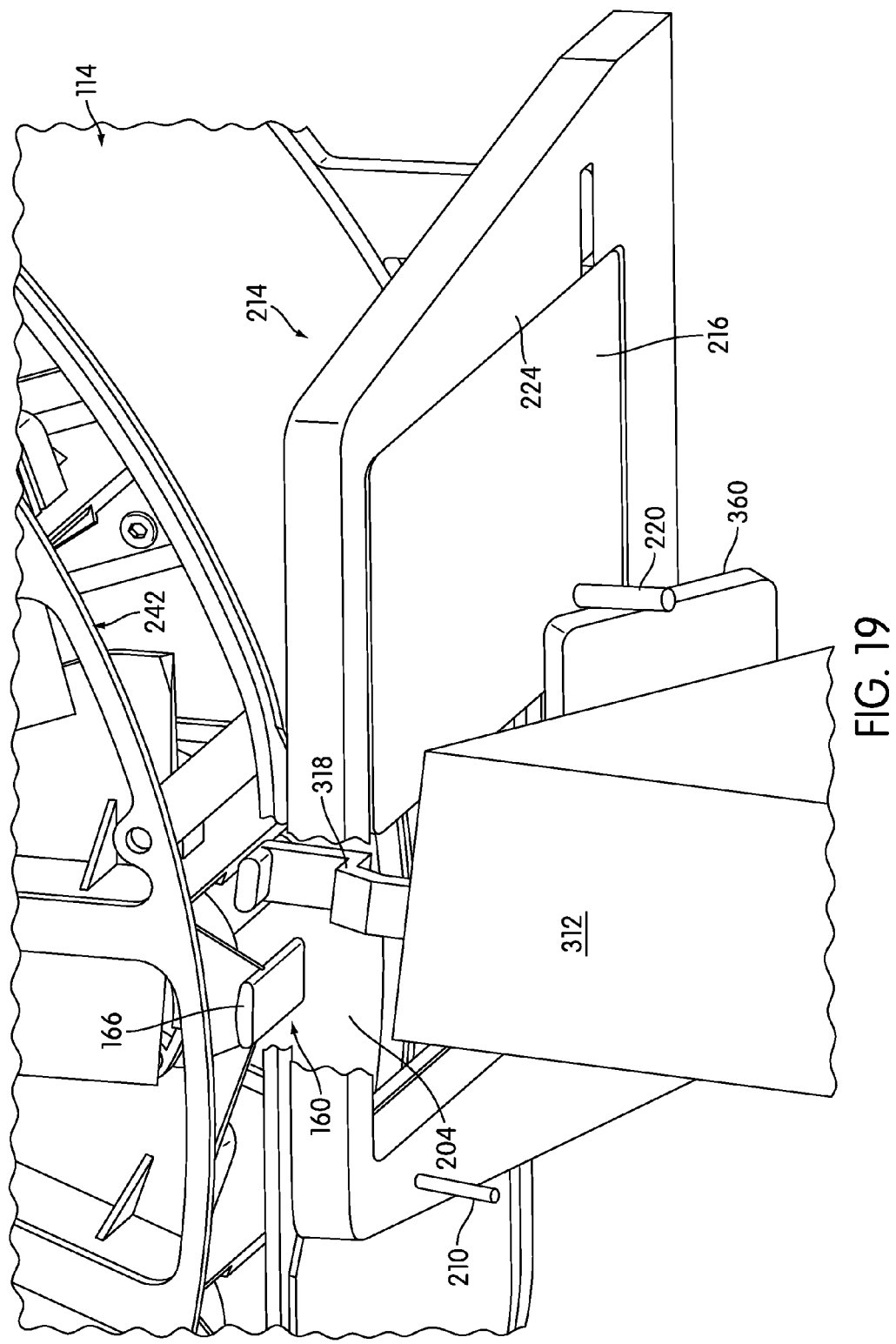
FIG. 19 is a partial perspective view of the incubator and a receptacle transport mechanism adapted to place reaction receptacles into the incubator and remove reaction receptacles from the incubator.

FIG. 19 shows a portion of a distribution head 312 extending a receptacle hook 318 into a receptacle portal 204 of a door assembly 214 of an incubator 114. The door assembly 214 includes an actuating post 220 extending from a door 216 that is slidably disposed within a door frame 224 so as to cover the portal 204 when in the closed position. The door engagement bracket 360 of the distribution head 312 engages the actuating post 220 to push the door 216 to an open position. With the door 216 in the open position, the receptacle hook 318 can be extended through the receptacle opening 204 to insert an MRD 160 into a receptacle carrier 242 (e.g., a carousel) within the incubator 114 or to retrieve an MRD 160 from the receptacle carrier 242.

Incubator 114 further includes a locator pin 210 projecting from the door frame 224 adjacent the receptacle portal 204. Pin 210, located at a known position with respect to the receptacle portal 204, functions as a position locator element for the incubator 114. By determining and storing the X, Z, Θ, and R coordinates at which the receptacle hook 318 contacts the pin 210, those coordinates can be recalled to properly position and orient the receptacle carrier assembly 310 and distribution head 312 when a receptacle needs to be placed in or removed from the incubator 114.

It should be noted that the door engagement bracket 360 shown in FIG. 19 is oriented differently than the door engagement bracket 360 shown in the other figures, such as FIG. 18, for example. In FIG. 19 the door engagement bracket 360 extends off the right-hand side of the distribution head 312 (when viewed in the direction of receptacle hook extension, as shown in FIG. 19) for opening the door 216 by pushing it to the right, as shown in FIG. 19. In FIG. 18, on the other hand, the door engagement bracket 360 extends off the left-hand side of the distribution head 312 (when viewed in the direction of receptacle hook extension, which is opposite to the viewing direction shown in FIG. 18) for opening a door by pushing it to the left. Thus, the distribution head 312 can be configured for opening module doors by pushing them to the left or the right, depending on the orientation of the door engagement bracket 360. A door engagement bracket can also be configured to extend on both the left-hand and right-hand sides of the distribution head 312, so that the head 312 can selectively push a door to the left or the right, so that all module doors need not be configured to open by sliding in the same direction. In other embodiments, the door may be opened by other than lateral movement. For example, the door may open by a pivoting, hinge-wise movement, by vertical movement, up or down, or by a rotating or revolving movement. The distribution head 312 can be configured to engage the door and making the appropriate relative movement to open the door.

Figure 20:
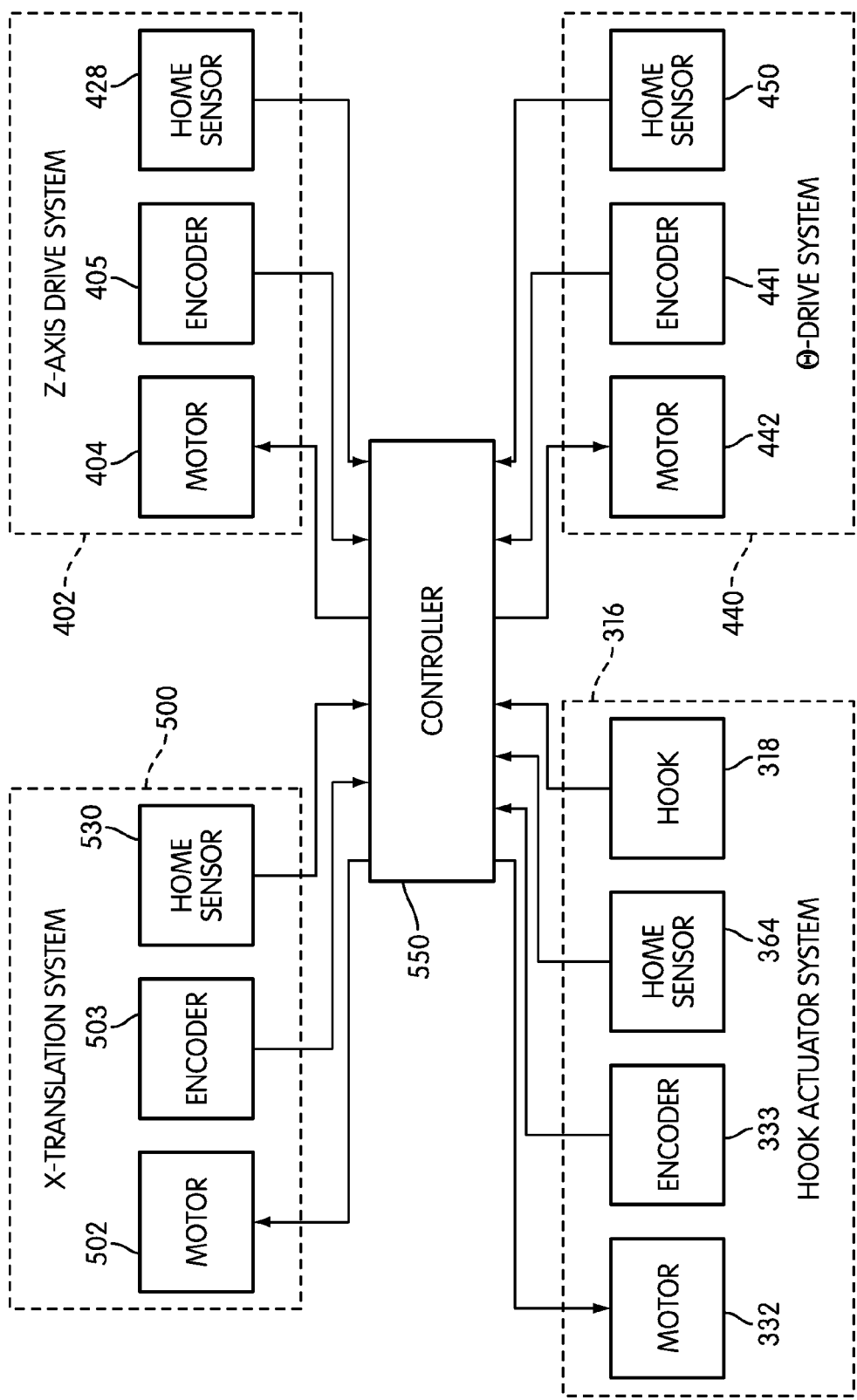
FIG. 20 is a schematic block diagram of the control architecture of the receptacle distributor.

FIG. 20 is a block diagram that schematically illustrates the control architecture for the receptacle distributor 300. The control architecture includes a controller 550 which communicates with and controls aspects of the X-translation system 500, the Z-axis drive system 402, the Θ-drive system 440, and the hook actuator system 316.

Controller 550 comprises a computer system for executing software that implements the methods and system of the current invention. Controller 550 includes at least one processor, e.g., a computer, and includes data storage memory, which may include random access memory (RAM), read only memory (ROM), and other types of memory known to those skilled in the art. Controller 550 may also include additional memory, including, for example, a hard disk drive and/or a removable storage drive, representing a magnetic tape drive, an optical disk drive, USB slot, memory card interface, etc. Memory devices and storage units used herein may comprise any storage medium for persistent and/or volatile storage of electronic data known to or developed by persons of ordinary skill in the art. Such data may be stored within the storage medium in a database, which may comprise any data structure and format known to or developed by persons of ordinary skill in the art, including, for example, a relational database, an object database, a flat file, list, and so on, or some combination thereof.

In alternative embodiments, some or all of the memory may include other similar means for allowing computer programs or other instructions to be loaded into a computer system. Such means can include, for example, a removable storage unit and an interface. Examples of such can include a memory stick and memory stick interface, a secure digital card and interface, and other portable media and interfaces which allow software and data to be transferred to controller 550.

The computer system of controller 550 may also include a communications interface, which allows information (e.g., software, data, etc.) to be transferred between controller 550 and external devices. Examples of communications interface can include a modem, a network interface (such as an Ethernet card), a communications port, a PCMCIA slot and card, a USB-port, a Firewire port, etc. Information transferred via a communications interface is in the form of signals which can be electronic, electromagnetic, optical or other signals capable of being received by the communications interface.

The computer system of controller 550 can also include one or more input devices, such as a touch screen, stylus, keyboard, mouse or other pointing device, microphone, and so on. Various output devices may also be included in the computer system, including indicator lights, a display, printer, and audio speakers.

In this document, terms such as "computer program medium," "computer-readable medium," "computer usable medium," and the like are used to generally refer to media, such as removable storage units, a hard disk installed in hard disk drive, or signals and other means for providing software and data to controller 550.

Computer programs (also called computer control logic) are stored in one or more portions of the memory of controller 550. Computer programs can also be received via a communications interface. Such computer programs, when executed, enable the computer system of controller 550 to perform aspects of the present invention.

In an embodiment in which aspects of the invention are implemented using software, the software may be stored in a computer program product and loaded into the computer system of controller 550 using a removable storage drive, a hard drive, an interface, and/or a communications interface. The control logic (software), when executed by the processor of the controller 550, causes the processor to perform functional aspects of the invention as described herein via the systems, devices, apparatuses, sensors, encoder, etc. described above. An operating system may perform basic tasks such as recognizing input from an input device, sending output to an output device, managing files and system resources, and managing the various processes embodying computer programs running on the computer system.

Controller 550 may comprise a stand-alone system dedicated to the receptacle distributor, or one or more components of controller 550—e.g., processor, memory, interfaces, input/output devices, etc.—may be a shared part of a global controller that controls one or more modules of the analyzer 100, in addition to the receptacle distributor 300.

As shown schematically in FIG. 20, with respect to the X-translation system 500, controller 550 receives signals from the optical encoder 503 coupled to motor 502 and from home sensor 530 and sends command signals to motor 502. With respect to the Z-axis drive system 402, controller 550 receives signals from the encoder 405 (e.g., slotted disc 432) coupled to ball screw 406 and from home sensor 428 and sends command signals to motor 404. With respect to the Θ-drive system 440, controller 550 receives signals from the encoder 441 coupled to motor 442 and from home sensor 450 and sends command signals to motor 442. And with respect to the hook actuator system 316, controller 550 receives signals from the encoder 333 coupled to motor 332, from home sensor 364, and from capacitive hook 318 and sends command signals to motor 332.

Figure 21:
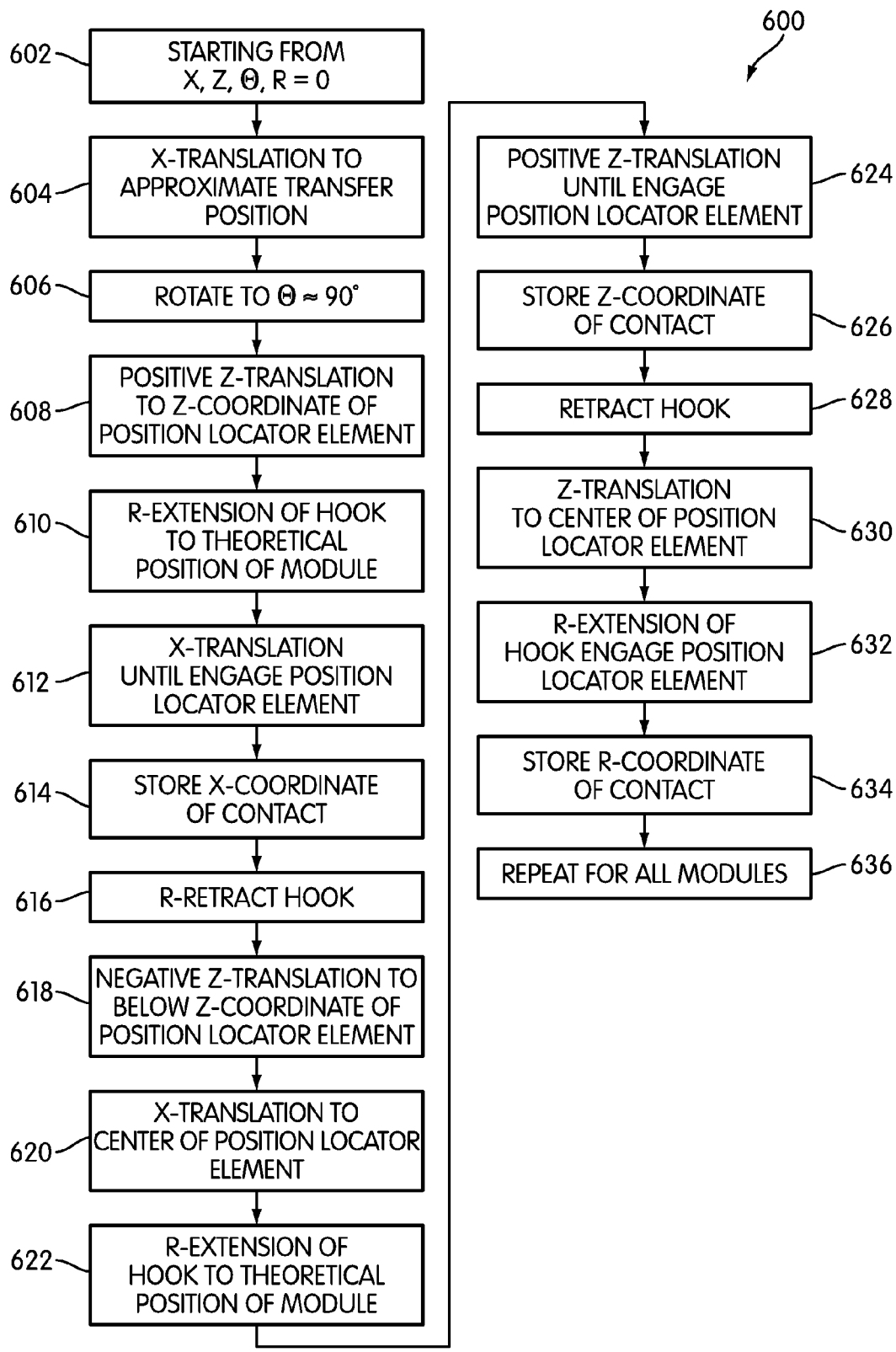
FIG. 21 is a flow chart illustrating the steps of a process by which the receptacle distributor automatically determines the coordinates of a receptacle transfer position with respect to each module of the instrument.

A process for automatically detecting the location coordinates of a receptacle transfer position with respect to the modules of the analyzer 100 is represented by flow chart 600 in FIG. 21. Some or all of the process shown can be embodied in computer instructions stored as software in memory accessible by the controller 550.

In step 602, the receptacle carrier assembly 310 starts from a position of X, Z, Θ, R=0, as communicated to the controller 550 by signals generated by the home sensor 530 of the X-translation system 500, by home sensor 428 of the Z-axis drive system 402, by home sensor 450 of the Θ-drive system 440, and by home sensor 364 of the hook actuator system 316.

In step 604, an approximate X-coordinate location of one of the analyzer modules is retrieved from the memory of the controller 550 by the controller's processor, and controller 550 sends command signals to motor 502 of the X-translation system 500 to move the carrier assembly 310 along the transport track assembly 458 in the X-direction to the approximate X-coordinate of the analyzer module. That the carrier assembly 310 is at the approximate X-coordinate can be verified by the command signals sent to the motor 502 (e.g., to move a specified number of steps) and/or by signals generated by the encoder 503.

In step 606, controller 550 commands motor 442 of the Θ-drive system 440 to rotate the distribution head 312, to an orientation of approximately 90 degrees so that the receptacle opening of the distribution head 312 faces the module. That the carrier assembly 310 is in the desired rotational orientation can be verified by the command signals sent to the motor 442 (e.g., to move a specified number of steps) and/or by signals generated by the encoder 441.

In step 608, controller 550 commands motor 404 of the Z-axis drive system 402 to move the distribution head 312 upwardly in the +Z-axis direction a specified distance (of, e.g., 5 mm to an absolute position of Z=+5 mm) That the carrier assembly 310 has moved the proper distance along the Z-axis can be verified by the command signals sent to the motor 404 (e.g., to move a specified number of steps) and/or by signals generated by the encoder 405.

In step 610, controller 550 commands motor 332 of the hook actuator system 316 to extend the hook 318 to a theoretical position of a position locator element (e.g., a pin or other projection extending from the module at a known position relative to the receptacle transfer position for that module). The theoretical position can be attained by moving the hook 318 a specified distance (e.g., 2 mm) toward the module, or, if the theoretical position varies significantly from module to module, the coordinates of the theoretical position can stored in the controller's memory and retrieved when necessary by the processor of the controller 550. That the hook 318 has extended to the desired position can be verified by the command signals sent to the motor 332 (e.g., to move a specified number of steps) and/or by signals generated by the encoder 333.

In step 612, controller 550 commands the motor 502 of the X-translation system 500 to move the receptacle carrier assembly 310 step-by-step in the X-axis towards the expected location of the position locator element until the hook 318 makes contact with the position locator element as detected by capacitive sensing and communicated to the controller 550. Controller 550 commands motor 502 to stop X-translation, and, in step 614, the X-coordinate of the contact, as determined by signals generated by the encoder 503 of the X-translation system 500, is stored in the memory of controller 550.

In step 616, controller 550 commands motor 332 of the hook actuator system 316 to retract the hook 318 into the distribution head 312.

In step 618, controller 550 commands motor 404 of the Z-axis drive system 402 to move the distribution head 312 downwardly in the −Z-axis direction to location known to be below the theoretical position of the position locator element. The distribution head can be moved a specified distance (e.g., a distance of 13 mm to an absolute Z=−8 mm), or, if the theoretical position varies significantly from module to module, the coordinates of the theoretical position can stored in the controller's memory and retrieved when necessary by the processor of the controller 550. The Z coordinate location of the distribution head is determined by signals generated by the encoder 405.

In step 620, the controller 550, using the stored results of steps 612 and 614, commands motor 502 of the X-translation system 500 to move the receptacle carrier assembly 310 in the X-direction to center the hook 618 with respect to the position locator element. This is accomplished by moving the receptacle carrier assembly 310 in the X-direction by a distance corresponding to half the width of the position locator element from the contact X-coordinate determined and stored in steps 612 and 614.

In step 622, controller 550 commands motor 332 of the hook actuator system 316 to extend the hook 318 to a theoretical position of the position locator element. Again, the theoretical position can be attained by moving the hook 318 a specified distance (e.g., 2 mm) toward the module, or, if the theoretical position varies significantly from module to module, the coordinates of the theoretical position can stored in the controller's memory and retrieved when necessary by the processor of the controller 550.

In step 624, controller 550 commands motor 404 of the Z-axis drive system 402 to move the receptacle distribution head 312 in the +Z-axis direction towards the expected location of the position locator element until the hook 318 makes contact with the position locator element as detected by capacitive sensing and communicated to the controller 550. Controller 550 commands motor 404 to stop Z-axis drive, and, in step 626, the Z-coordinate of the contact, as determined by signals generated by the encoder 405 of the Z-axis drive system 402, is stored in the memory of controller 550.

In step 628, controller 550 commands motor 332 of the hook actuator system 316 to retract the hook 318 into the distribution head 312.

In step 630, the controller 550, using the stored results of steps 624 and 626, commands motor 404 of the Z-axis drive system 402 to move the distribution head 312 in the Z-direction to center the hook 618 with respect to the position locator element.

In step 632, controller 550 commands motor 332 of the hook actuator system 316 to move the hook 318, in the R-direction, toward the position locator element until hook 318 makes contact with the position locator element as detected by capacitive sensing and communicated to the controller 550. Controller 550 commands motor 332 to stop hook extension, and, in step 634, the R-coordinate of the contact, as determined by signals generated by encoder 333 of the hook actuator system 316, is stored in the memory of controller 550.

In step 636, this procedure (at least steps 604-634) is repeated for all modules, and the receptacle transfer coordinates of each are stored. Thus, when the receptacle distributor 300 is required to transfer a receptacle into or out of a receptacle receiving structure (i.e., module), the X and Z coordinates of the receptacle transfer position for that module are retrieved by the controller 550, and the X-translation system 500 and the Z-axis drive system 402 are commanded by the controller to position the distribution head 312 at the proper X and Z coordinates, respectively. Similarly, the R-coordinate for the receptacle transfer position is retrieved by the controller 550, which uses the information to effect proper extension of hook 318 via hook actuator system 316 for placing the receptacle into the module or removing the receptacle from the module.

While the invention has been described in connection with what is presently considered to be the most practical and preferred embodiments, it is to be understood that the invention is not to be limited to the disclosed embodiments, but, on the contrary, it is intended to cover various modifications and equivalent arrangements included within the spirit and scope of the appended claims. Thus, it is to be understood that variations in the particular parameters used in defining the present invention can be made without departing from the novel aspects of this invention as defined in the following claims.

The invention claimed is:

1. An apparatus for transferring one or more receptacles between a plurality of receptacle-receiving structures comprising:
   a transport track having opposed ends, wherein the receptacle-receiving structures are disposed at different locations adjacent to said transport track;
   a receptacle carrier operatively engaged with said transport track and adapted to carry a receptacle and translate along said transport track in a first or second direction between said opposed ends, wherein said receptacle carrier is further adapted to selectively stop at a transfer position with respect to any of the receptacle-receiving structures disposed adjacent said transport track, and wherein said receptacle carrier includes a receptacle moving mechanism adapted to move a receptacle with respect to said receptacle carrier to move a receptacle into said receptacle carrier, move a receptacle out of said receptacle carrier, or alternately move a receptacle into and out of said receptacle carrier;
   a transfer position locating system adapted to automatically determine, for each receptacle-receiving structure, a location of a transfer position of the receptacle carrier with respect to the receptacle-receiving structure to enable the receptacle carrier to transfer a receptacle between the receptacle carrier and the receptacle-receiving structure; and a carrier elevation system adapted to move at least a portion of said receptacle carrier in a transverse direction with respect to said transport track.

2. The apparatus of claim 1, wherein said transport track comprises a base portion and an upright backing portion and a guide track mounted on said base portion and a guide rail mounted to said upright portion, wherein a portion of said receptacle carrier is engaged with said guide track and said guide rail.

3. The apparatus of claim 1, wherein said transport track is linear.

4. The apparatus of claim 1, wherein said transport track is substantially horizontal.

5. The apparatus of claim 1, further comprising a carrier translation system adapted to effect powered translation of said receptacle carrier along said transport track.

6. The apparatus of claim 5, wherein said carrier translation system comprises:
a translation drive motor having an output shaft;
a carrier drive belt coupled to said receptacle carrier; and
one or more pulleys supporting said carrier drive belt,
wherein said carrier drive belt is coupled to said output shaft of said translation drive motor so that rotation of said output shaft is transmitted via said carrier drive belt into translation of said receptacle carrier along said transport track.

7. The apparatus of claim 6, further comprising an encoder coupled to said translation drive motor for monitoring rotations of said output shaft.

8. The apparatus of claim 6, further comprising a belt tensioner configured to impart tension in said carrier drive belt.

9. The apparatus of claim 1, further comprising a carrier position sensor configured to detect when said receptacle carrier is in a specified position on said transport track.

10. The apparatus of claim 1, wherein said transport track is substantially horizontal and wherein said carrier elevation system is adapted to move at least a portion of said receptacle carrier in a vertical direction with respect to said transport track.

11. The apparatus of claim 1, wherein said carrier elevation system comprises:
an elevation drive motor having an output shaft;
a drive screw shaft having a longitudinal axis and operatively coupled to said elevation drive motor for powered rotation of said drive screw shaft; and
an elevation block coupled to said drive screw shaft such that rotation of said drive screw shaft causes translation of said elevation block along the longitudinal axis of said drive screw shaft,
wherein at least a portion of said receptacle carrier is carried on said elevation block.

12. The apparatus of claim 11, further comprising an encoder coupled to said elevation drive motor for monitoring rotations of said output shaft.

13. The apparatus of claim 1, further comprising a elevation position sensor configured to detect when at least a portion of said receptacle carrier is in a specified transverse distance from said transport track.

14. The apparatus of claim 1, further comprising a carrier rotation system adapted to rotate at least a portion of said receptacle carrier about an axis of rotation.

15. The apparatus of claim of claim 14, wherein said transport track is substantially horizontal and wherein said axis of rotation is substantially vertical.

16. The apparatus of claim 14, wherein said carrier rotation system comprises:
a rotation drive motor having an output shaft;
a drive gear coupled to said output shaft; and
a platform gear mounted so as to be rotatable about said axis of rotation and coupled to said drive gear for powered rotation to said platform gear,
wherein at least a portion of said receptacle carrier is carried on said platform gear.

17. The apparatus of claim 16, further comprising an encoder coupled to said rotation drive motor for monitoring rotations of said output shaft.

18. The apparatus of claim 14, further comprising a rotation position sensor configured to detect when at least a portion of said receptacle carrier is in a specified rotational position about said axis of rotation.

19. The apparatus of claim 1, wherein said receptacle moving mechanism comprises:
a receptacle engagement device configured to releasably engage a receptacle to permit physical manipulation of the engaged receptacle; and
a receptacle drive motor having an output shaft coupled to said receptacle engagement device for effecting powered movement of said receptacle engagement device.

20. The apparatus of claim 19, wherein said receptacle engagement device comprises a hook.

21. The apparatus of claim 19, wherein said receptacle engagement device is carried on an engagement device carriage, and wherein said receptacle moving mechanism further comprises:
a receptacle guide rail on which said engagement device carriage is translatably carried;
a receptacle drive belt coupled to said engagement device carriage; and
one or more pulleys supporting said receptacle drive belt,
wherein said receptacle drive belt is coupled to said output shaft of said receptacle drive motor so that rotation of said output shaft is transmitted via said receptacle drive belt into translation of said engagement device carriage along said receptacle guide rail.

22. The apparatus of claim 19, further comprising an encoder coupled to said receptacle drive motor for monitoring rotations of said output shaft.

23. The apparatus of claim 21, further comprising a belt tensioner configured to impart tension to said receptacle drive belt.

24. The apparatus of claim 21, further comprising an engagement device position sensor configured to detect when said engagement device carriage is in a specified position on said receptacle guide rail.

25. The apparatus of claim 1, wherein said receptacle carrier comprises:
a receptacle carrier carriage adapted to translate along said transport track; and
a distribution head supported by said receptacle carrier carriage and configured to receive and hold a receptacle and wherein said receptacle moving mechanism is disposed within said distribution head.

26. The apparatus of claim 25, further comprising a carrier translation system coupled to said receptacle carrier carriage and adapted to effect powered translation of said receptacle carrier carriage along said transport track.

27. The apparatus of claim 25, wherein the carrier elevation system is coupled to said distribution head and adapted to move said distribution head relative to said receptacle carrier carriage in a direction transverse to said transport track.

28. The apparatus of claim 25, wherein the carrier rotation system is coupled to said distribution head and adapted to rotate said distribution head relative to said receptacle carrier carriage about an axis of rotation.

29. The apparatus of claim 1, wherein said transfer position locating system comprises:
   a position locator element associated with said receptacle carrier;
   one or more signal generators adapted to generate signal data representative of at least one of a position and an orientation of said receptacle carrier; and
   data storage configured to store signal data from said one or more signal generators when said position locator element associated with said receptacle carrier engages a position locator element associated with the receptacle-receiving structure.

30. The apparatus of claim 29, wherein said position locator element associated with said receptacle carrier comprises a portion of the receptacle carrier that physically contacts a position locator element associated with the receptacle-receiving structure.

31. The apparatus of claim 29, wherein said position locator element associated with said receptacle carrier comprises a receptacle engagement device coupled with said receptacle moving mechanism and configured to releasably engage a receptacle to permit physical manipulation of the engaged receptacle.

32. The apparatus of claim 31, further comprising a controller in signal communication with said receptacle engagement device to capacitively sense when the receptacle engagement device contacts the position locator element associated with the receptacle-receiving structure.

33. A method for transferring one or more receptacles between a plurality of receptacle receiving structures in an automated apparatus comprising a receptacle carriage, a plurality of receptacle-receiving structures, and a transport track, said method comprising the steps of:
   (a) moving the receptacle carriage along the track to an approximate location of one of the receptacle-receiving structures;
   (b) moving the receptacle carriage with respect to the receptacle-receiving structure in two or more directions until a position locator element associated with the receptacle carriage engages a position locator element associated with the receptacle-receiving structure, wherein engagement of the position locator element associated with the receptacle carriage with the position locator element associated with the receptacle-receiving structure identifies a transfer position of the receptacle carriage with respect to the receptacle-receiving structure to enable the receptacle carriage to transfer a receptacle between the receptacle carriage and the receptacle-receiving structure;
   (c) storing data relating to the transfer position for the receptacle-receiving structure;
   (d) repeating steps (a)-(c) for each of the receptacle-receiving structures; and
   (e) positioning the receptacle carriage with respect to each receptacle-receiving structure to enable the receptacle carriage to transfer a receptacle between the receptacle carriage and the receptacle-receiving structure by retrieving the stored transfer position data associated with a receptacle-receiving structure and moving the receptacle carriage to the transfer position defined by the retrieved transfer position data.

34. The method of claim 33, wherein moving the receptacle carriage with respect to the receptacle-receiving structure in two or more directions comprises moving the receptacle carriage along the track and moving the receptacle carriage in at least one direction transverse to the direction of the track.

35. The method of claim 33, wherein moving the receptacle carriage with respect to the receptacle-receiving structure in two or more directions further comprises rotating the receptacle carriage about an axis of rotation and moving a receptacle-engaging element of the receptacle carriage in a radial direction with respect to the axis of rotation.

36. The method of claim 33, wherein moving the receptacle carriage with respect to the receptacle-receiving structure until a position locator element associated with the receptacle carriage engages a position locator element associated with the receptacle-receiving structure comprises moving the receptacle carriage with respect to the receptacle-receiving structure until a portion of the receptacle carriage physically contacts a portion of the receptacle-receiving structure.

37. The method of claim 36, wherein physical contact of a portion of the receptacle carriage with a portion of the receptacle-receiving structure is determined by capacitive sensing.

38. An apparatus for transferring one or more receptacles between a plurality of receptacle-receiving structures, one or more of the receptacle receiving structures including a receptacle transfer portal through which a receptacle is placed into or removed from the receptacle-receiving structure and a door disposed over the receptacle transfer portal, said apparatus comprising:
   a receptacle carriage adapted to carry a receptacle and to selectively stop at a transfer position with respect to any of a plurality of receptacle-receiving structures, one or more of the receptacle receiving structures including a receptacle transfer portal, and wherein said receptacle carriage includes a receptacle moving mechanism adapted to move a receptacle with respect to said receptacle carriage to move a receptacle into said receptacle carriage, move a receptacle out of said receptacle carriage, or alternately move a receptacle into and out of said receptacle carriage,
   wherein a portion of said receptacle carriage is adapted to engage a door of a receptacle-receiving structure and to open the door upon performance of a predetermined movement of said receptacle carriage with respect to the receptacle-receiving structure; and
   a carriage positioning system adapted to automatically position said receptacle carriage so that a portion of said receptacle carriage engages a door of a selected one of the receptacle-receiving structures and to effect the predetermined movement of said receptacle carriage to open the door.

39. The apparatus of claim 38, further comprising a transfer position locating system adapted to automatically determine, for each receptacle-receiving structure, a location of a transfer position of the receptacle carriage with respect to the receptacle-receiving structure to enable the receptacle carriage to engage a door of each receptacle-receiving structure.

40. The apparatus of claim 39, wherein said transfer position locating system comprises:
   a position locator element associated with said receptacle carriage;
   one or more signal generators adapted to generate signal data representative of at least one of a position and an orientation of said receptacle carriage; and
   data storage configured to store signal data from said one or more signal generators when said position locator element associated with said receptacle carriage engages a position locator element associated with the receptacle-receiving structure.

41. The apparatus of claim 38, wherein the portion of said receptacle carriage adapted to engage the door of the receptacle-receiving structure comprises a bracket projecting from said receptacle carriage and configured to engage by contact an actuating element extending from the door.

42. The apparatus of claim 38, wherein a portion of said receptacle carriage is adapted to engage a door of a receptacle-receiving structure and to open the door upon performance of a lateral movement of said receptacle carriage to move the door laterally from a closed position to an open position with respect to the receptacle transport portal.

43. The apparatus of claim 38, wherein a portion of said receptacle carriage is adapted to remain engaged with the door of the receptacle-receiving structure after the predetermined movement of said receptacle carriage to hold the door in an open position with respect to the receptacle transport portal while the receptacle carriage moves a receptacle through the receptacle transport portal.

44. A method of opening a door in an automated apparatus comprising a plurality of receptacle receiving structures and a receptacle carriage, wherein one or more of the receptacle receiving structures includes a receptacle transfer portal through which a receptacle is placed into or removed from the receptacle-receiving structure and a door disposed over the receptacle transfer portal, said method comprising the steps of:
  positioning the receptacle carriage so that a portion of the receptacle carriage adapted to engage a door of a receptacle-receiving structure and to open the door upon performance of a predetermined movement of the receptacle carriage with respect to the receptacle-receiving structure engages a door of a selected one of the receptacle-receiving structures; and
  effecting the predetermined movement of the receptacle carriage to open the door.

45. The method of claim 44, wherein positioning the receptacle carriage comprises the steps of:
  (a) moving the receptacle carriage to an approximate location of one of the receptacle-receiving structures;
  (b) moving the receptacle carriage with respect to the receptacle-receiving structure in two or more directions until a position locator element associated with the receptacle carriage engages a position locator element associated with the receptacle-receiving structure, wherein engagement of the position locator element associated with the receptacle carriage with the position locator element associated with the receptacle-receiving structure identifies a transfer position of the receptacle carriage with respect to the receptacle-receiving structure to enable the receptacle carriage to engage a door of the receptacle-receiving structure;
  (c) storing data relating to the transfer position for the receptacle-receiving structure;
  (d) repeating steps (a)-(c) for each of the receptacle-receiving structures; and
  (e) positioning the receptacle carriage with respect to each receptacle-receiving structure to enable the receptacle carriage to engage the door of each receptacle carriage by retrieving the stored transfer position data associated with a receptacle-receiving structure and moving the receptacle carriage to the transfer position defined by the retrieved transfer position data.

46. The method of claim 44, wherein the portion of the receptacle carriage adapted to engage the door of the receptacle-receiving structure comprises a bracket projecting from the receptacle carriage and configured to engage by contact an actuating element extending from the door, and positioning the receptacle carriage comprises moving the receptacle carriage to a position at which the bracket engages the actuating element of the door.

47. The method of claim 44, wherein effecting the predetermined movement comprises moving the receptacle carriage laterally to move the door laterally from a closed position to an open position with respect to the receptacle transport portal.

48. The method of claim 44, further comprising, after effecting the predetermined movement, maintaining a position of the receptacle carriage engaged with the door of the receptacle-receiving structure to hold the door in an open position with respect to the receptacle transport portal while the receptacle carriage moves a receptacle through the receptacle transport portal.

* * * * *